US009604950B2

(12) United States Patent
Kravchenko et al.

(10) Patent No.: US 9,604,950 B2
(45) Date of Patent: Mar. 28, 2017

(54) TRAIL ENHANCERS FOR THE SELECTIVE KILLING OF CANCER CELLS

(71) Applicant: The Scripps Research Institute, La Jolla, CA (US)

(72) Inventors: Vladimir Kravchenko, San Diego, CA (US); Richard J. Ulevitch, La Jolla, CA (US); Kim D. Janda, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/778,327

(22) PCT Filed: Mar. 19, 2014

(86) PCT No.: PCT/US2014/031235
§ 371 (c)(1),
(2) Date: Sep. 18, 2015

(87) PCT Pub. No.: WO2014/153415
PCT Pub. Date: Sep. 25, 2014

(65) Prior Publication Data
US 2016/0272603 A1   Sep. 22, 2016

Related U.S. Application Data

(60) Provisional application No. 61/803,177, filed on Mar. 19, 2013.

(51) Int. Cl.
*C07D 307/04*    (2006.01)
*C07D 307/34*    (2006.01)
*C07D 307/33*    (2006.01)
*A61K 31/396*    (2006.01)
*A61K 31/365*    (2006.01)
*A61K 38/17*     (2006.01)
*C07D 405/12*    (2006.01)
*A61K 31/337*    (2006.01)
*A61K 31/341*    (2006.01)
*A61K 38/19*     (2006.01)
*C07D 305/12*    (2006.01)

(52) U.S. Cl.
CPC .......... *C07D 307/33* (2013.01); *A61K 31/337* (2013.01); *A61K 31/341* (2013.01); *A61K 31/365* (2013.01); *A61K 31/396* (2013.01); *A61K 38/177* (2013.01); *A61K 38/19* (2013.01); *C07D 305/12* (2013.01); *C07D 405/12* (2013.01)

(58) Field of Classification Search
USPC ....................................................... 549/429
See application file for complete search history.

(56) References Cited

U.S. PATENT DOCUMENTS

| 6,602,905 B1 | 8/2003 | Gardiner et al. |
| 2004/0259942 A1 | 12/2004 | Shaw et al. |
| 2005/0003387 A1 | 1/2005 | Aza-Blanc et al. |
| 2007/0010477 A1 | 1/2007 | Dolnick et al. |
| 2007/0010488 A1 | 1/2007 | Youssef et al. |
| 2010/0286261 A1 | 11/2010 | Pritchard et al. |

FOREIGN PATENT DOCUMENTS

| CN | 102482244 A | 5/2012 |
| CN | 105228618 A | 1/2016 |
| JP | 2016515546 A | 5/2016 |
| WO | WO-2011001419 A1 | 1/2011 |
| WO | WO-2014/153415 A2 | 9/2014 |
| WO | WO-2014/153415 A3 | 9/2014 |

OTHER PUBLICATIONS

Kravchenko et al., ACS Chemical Biology (2013), 8(6), 1117-1120.*
"International Application Serial No. PCT/US2014/031235, International Search Report mailed Nov. 7, 2014", 4 pgs.
"International Application Serial No. PCT/US2014/031235, Invitation to Pay Additional Fees and Partial Search Report mailed Jul. 30, 2014", 2 pgs.
"International Application Serial No. PCT/US2014/031235, Written Opinion mailed Nov. 7, 2014", 6 pgs.
Dubinsky, et al., "Species selective diazirine positioning in tag-free photoactive quorum sensing probes", Chem Commun 49(52):, (2013), 5826-5828.
Karlsson, et al., "The Pseudomonas aeruginosa N-Acylhomoserine Lactone Quorum Sensing Molecules Target IQGAP1 and Modulate Epithelial Cell Migration", PLOS Pathogen 8(10):, (1-17,2014), 17 pgs.
Kravchenko, et al., "Facilitating Cytokine-Mediated Cancer Cell Death by Proteobacterial N-Acylhomoserine Lactones", ACS Chem. Biol. 8(6):, [Online]. Retrieved from the Internet: <URL: http://pubs.acs.org/doi/abs/10.1021/cb4000184>, (Oct. 8, 2014), 1117-1120.
Praneenararat, et al., "Chemical methods to interrogate bacterial quorum sensing pathways", Org Biomol Chem. 10(41), [Online]. Retrieved from the Internet: <URL: http://www.ncbi.nlm.nih.gov/pmc/articles/PMC3480174/pdf/nihms409202.pdf>, (Jul. 18, 2014), 8189-8199.
"International Application Serial No. PCT/US2014/031235, International Preliminary Report on Patentability mailed Oct. 1, 2015", 8 pgs.
"Chinese Application Serial No. 201480028681.0, Office Action mailed Oct. 18, 2016", with English translation of claims, 13 pgs.

(Continued)

*Primary Examiner* — Niloofar Rahmani
(74) *Attorney, Agent, or Firm* — Schwegman Lunberg & Woessner, P.A.

(57) ABSTRACT

The invention is directed to methods of inducing apoptosis, arresting cell cycle, or inhibiting cellular proliferation, or any combination thereof, in a tumor cell, by administration of an effective amount of an N-acyl homoserine lactone analog (AHL), optionally in conjunction with a tumor modulating agent such tumor necrosis factor (TNF) related apoptosis inducing ligand (TRAIL) to the patient. Novel bioactive analogs of an N-acyl homoserine lactone are also provided.

16 Claims, 16 Drawing Sheets

(56) References Cited

OTHER PUBLICATIONS

Garner, Amanda, et al., "Synthesis of 'clickable' acylhomoserine lactone quorum sensmg probes: Unanticipated effects on mammalian cell activation", Bioorg. Med. Chem. Lett., (May 1, 2011), 2702-2705.

"Chinese Application Serial No. 201480028681.0, Office Action mailed Oct. 18, 2016", (w/ English Translation), 13 pgs.

"Chinese Application Serial No. 201480028681.0, Response filed Nov. 14, 2016 to Office Action mailed Oct. 18, 2016", (w/ English Translation of Claims), 18 pgs.

"European Application Serial No. 14770705.3, Extended European Search Report mailed Oct. 17, 2016", 7 pgs.

Dubinsky, Luba, "Synthesis and validation of a probe to identify quorum sensing receptors", *Chemical Communications (Camb.)*, (No. 47). (2009), 7378-7380.

Garner, Amanda L, et al., "Synthesis of 'clickable' acylhomoserine lactone quorum sensing probes: Unanticipated effects on mammalian cell activation", *Bioorganic & Medicinal Chemistry Letters*, vol. 21, No. 9, (May 2011), 2702-2705.

\* cited by examiner

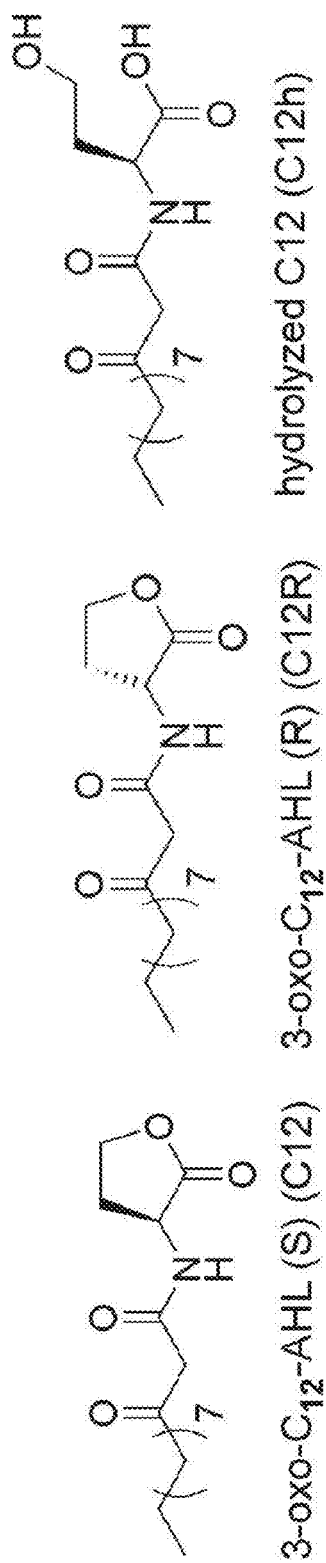

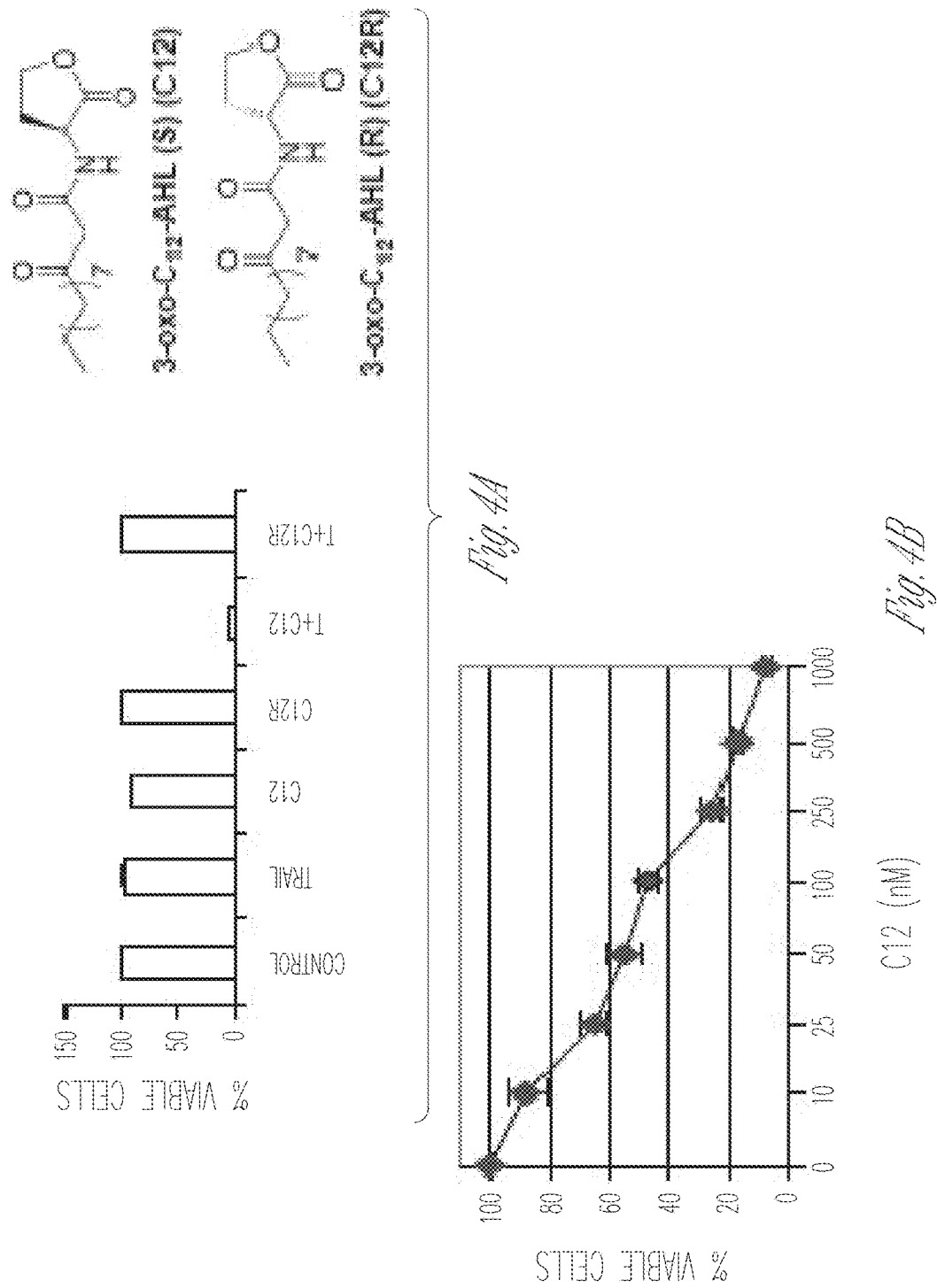

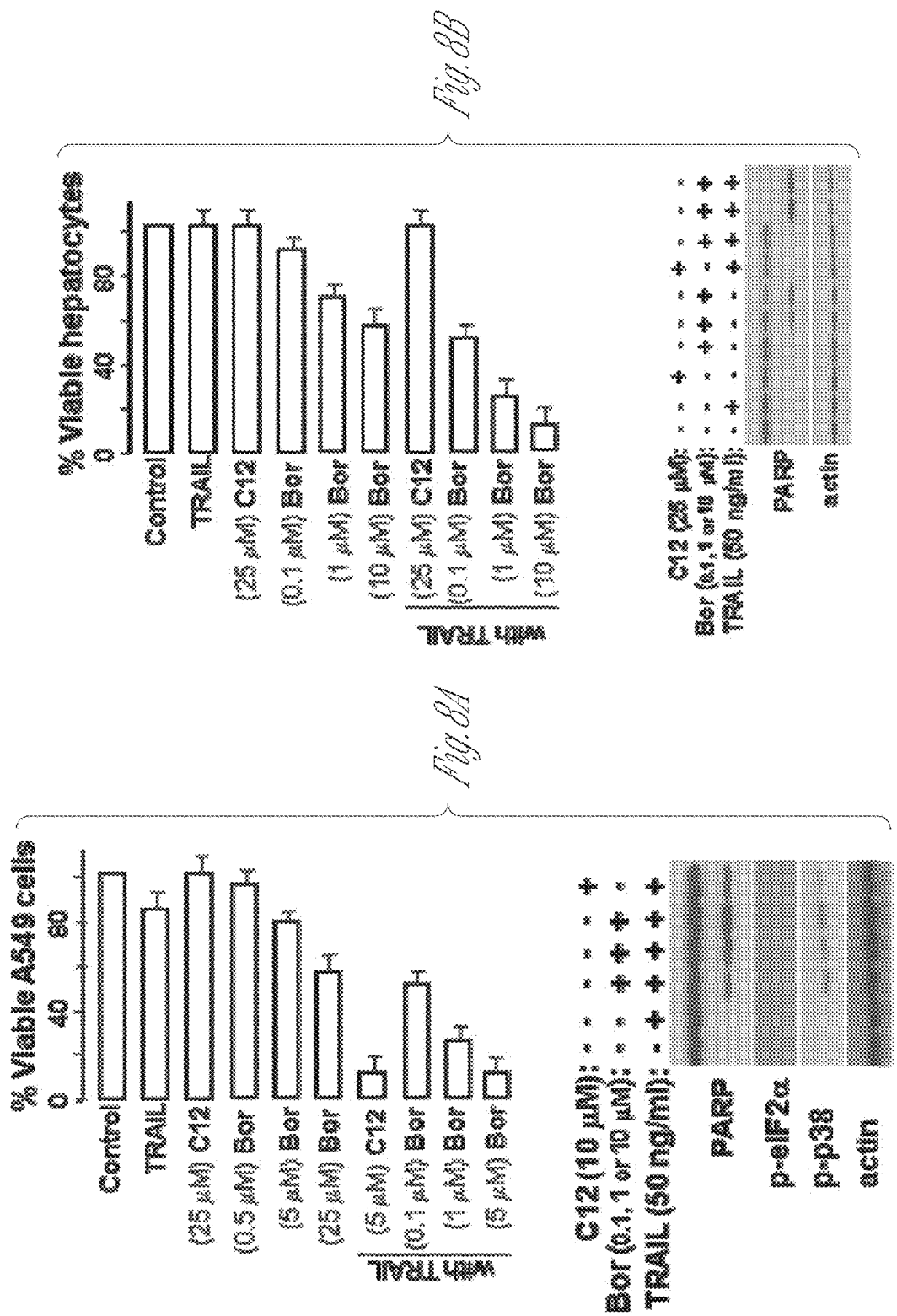

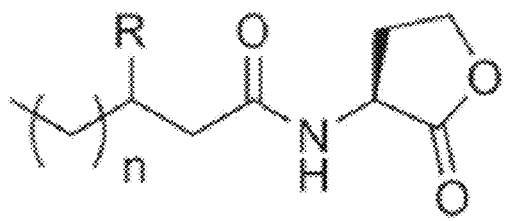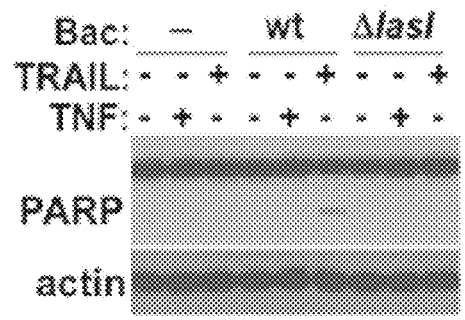
Fig. 11A    Fig. 11B
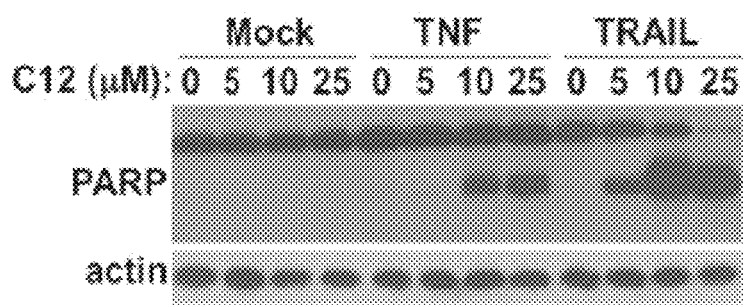
Fig. 11C
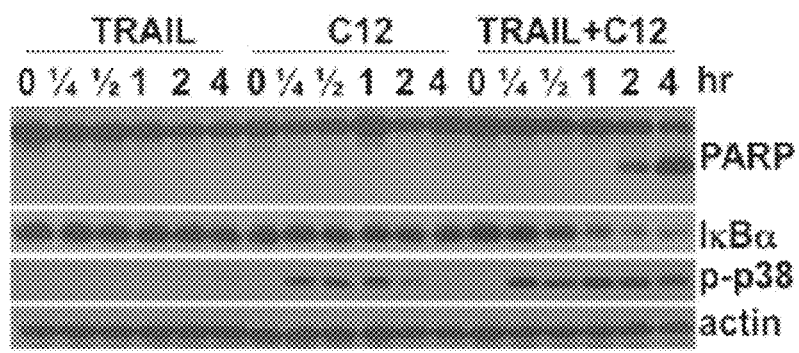
Fig. 11D

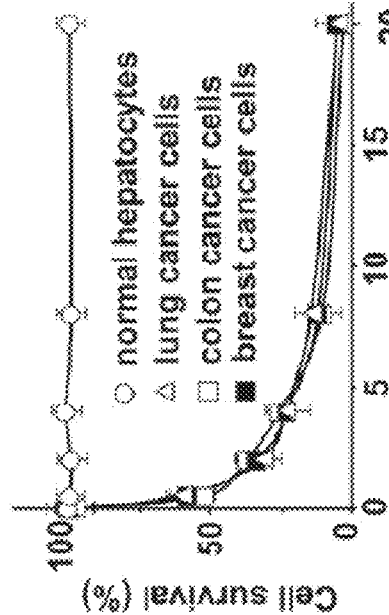
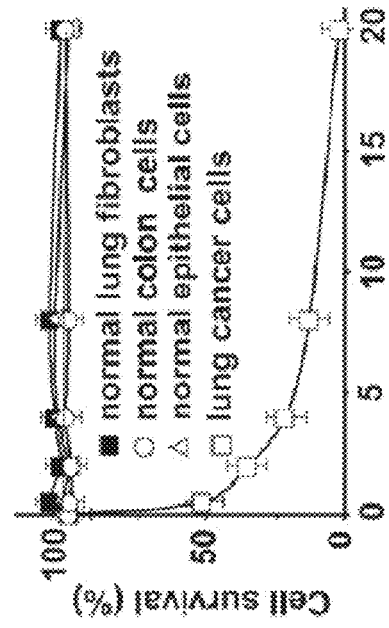
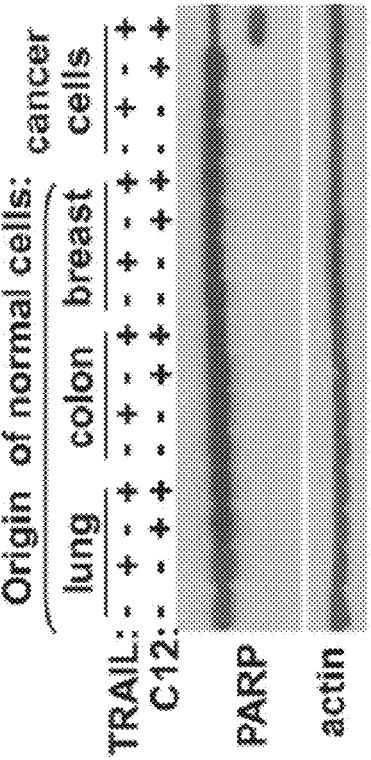

TRAIL ENHANCERS FOR THE SELECTIVE KILLING OF CANCER CELLS

CROSS-REFERENCE TO RELATED APPLICATIONS

This application is a U.S. national stage application filed under 35 U.S.C. §371 from International Application Serial No. PCT/US2014/031235, which was filed 19 Mar. 2014, and published as WO 2014/153415 on 25 Sep. 2014, and which claims the benefit of priority of U.S. provisional application Ser. No. 61/803,177, filed 19 Mar. 2013, which applications and publication are incorporated by reference as if reproduced herein and made a part hereof in their entirety, and the benefit of priority of each of which is claimed herein.

STATEMENT OF GOVERNMENT SUPPORT

This invention was made with government support under HHSN27200700038C, AI077644, AI079436, and AI094348, awarded by the National Institutes of Health. The U.S. government has certain rights in the invention.

BACKGROUND

Apoptosis is a genetically programmed and physiologically important form of cell death. It is a conserved cellular homeostatic mechanism with important roles in normal development through maintaining of cell turn-over in healthy adult tissues. Abnormal apoptotic activity has been linked to the pathogenesis of autoimmune and infectious disorders, including persistent inflammatory diseases (Gyrd-Hansen, et al., *Nat Rev Cancer* 10(8) 561-74). Evading apoptosis has also been identified as a hallmark of cancer (Hanahan D., et al., *Cell* 2000, 100(1), 57-70). Therefore, triggering apoptotic processes may be important for killing cancer cells and sensitizing them to different therapeutic regimens (Ashkenazi, A., *Nat Rev Drug Discov* 2008, 7(12), 1001-12; Ashkenazi, A, et al., *J Clin Invest* 1999, 104(2), 155-62).

Among promising candidates for cancer therapeutics is tumor necrosis factor (TNF) related apoptosis inducing ligand (TRAIL) initiated apoptosis through the receptor-mediated mechanism, also referred to as the extrinsic apoptotic pathway. In contrast to the naturally occurring pro-apoptotic ligands such as TNF and Fax ligand (FasL), TRAIL infusion into mice does not cause a lethal response or detectable toxicity to tissues and organs (Ashkenazi, A., *Nat Rev Drug Discov* 2008, 7(12), 1001-12; Ashkenazi, A, et al., *J Clin Invest* 1999, 104(2), 155-62; Walczak, H. et al., *Nat Med* 1999, 5(2), 157-63). Furthermore, the potential significance of TRAIL for killing cancer cells has been supported by studies in animal models demonstrating that this cytokine possesses selective toxicity to human tumor xenografts but not normal tissues. However, sensitivity to TRAIL-induced apoptosis is a key factor limiting the efficacy of TRAIL treatment, because a spectrum of sensitivity is observed in different malignant cells (Lippa, M. S. et al., *Apoptosis* 2007, 12(8), 1465). Furthermore, similar to normal cells, some cancer cells are also resistant to TRAIL-induced apoptosis.

The increasing understanding of the molecular details of apoptosis indicates that tumor cells can acquire resistance to apoptosis through interference with either extrinsic or intrinsic apoptotic signaling pathways. However, most cancer cells retain the capacity to undergo apoptosis if triggered through mechanisms that can overcome anti-apoptotic influences. For example, inhibition of NF-κB activity significantly increases apoptosis induced by apoptotic stimuli (Beg. A. A., et al, *Science* 1996, 274 (5288), 782-4; Wang, C. Y., et al., *Science* 1996, 274 (5288), 784-7; Van Antwerp, D. J., et al., *Science* 1996, 274 (5288), 787-9; Liu, Z. G., et al., *Cell* 1996, 87(3), 565-76). In addition, enhancing apoptosis also occurs upon activation of several intracellular non-apoptotic signaling processes, including the JNK pathway or endoplasmic reticular (ER) stress, known in eukaryotic cells as the unfolded protein response (UPR) (Ron, D. et al., *Nat Rev Mol Cell Biol* 2007, 8(7), 519-29). It has been observed that UPR activators such as tunicamycin, thapsigargin and RRR-α-tocopherol ether-link acetic acid analog (α-TEA), senstivize cancer cells to TRAIL-inducing apoptosis (Jiang, C. C., et al., *Cancer Res* 2007, 67(12), 5880; Chen, L. H. et al., *Carcinogenesis* 2007, 28(11), 2328-36; Tiwary, R., et al., *PLoS One* 5(7), e11865). However, these reagents induce constitutive and sustained activation of the UPR.

Bacterial metabolites play important roles in inflammation-mediated processes essential for normal development and the pathogenesis of numerous chronic diseases, including cancer. Inflammation is typically initiated as an innate immune response to specific bacterial products through receptor-dependent mechanisms, in which induction of the transcription factor NF-κB is required for both activation of the immune system and the control of apoptosis in activated cells. For example, in the presence of Gram-negative bacteria, NF-κB activation is initially induced in response to bacterial lipopolysaccharide (LPS), an agonist of the Toll-like receptor 4 (TLR4), leading to the expression of NF-κB-regulated genes encoding pro-inflammatory cytokines, such as tumor necrosis factor-α (TNF) and interlekin-1 (IL-1). After the engagement of TNF or IL-1 receptors, additional rounds of NF-κB activation amplify this LPS-induced inflammatory response. NF-κB-dependent processes, in concert with other signaling pathways, up-regulate the expression of pro-apoptotic cancer immunosurveillance effectors, including the TNF-related apoptosis-inducing ligand (TRAIL), an essential mediator of apoptotic cell death particularly in cancer cells. Although the LPS-induced inflammatory response results in the release of pro-apoptotic cytokines such as TNF and TRAIL, cancer cells receiving these death signals can still survive due to the suppressive effects of NF-κB signaling on apoptosis.

SUMMARY

The invention is directed in various embodiments to method of inducing apoptosis, arrest of cell division, or inhibition of cell proliferation, or any combination thereof, in a tumor cell. Tumor necrosis factor-related apoptosis-inducing ligand (TRAIL) preferentially induces apoptosis in cancer cells over normal cells; however, tumor cells may develop TRAIL resistance. Here we demonstrate that this resistance can be overcome in the presence of bacterial acylhomoserine lactone (AHL) analogs or AHL-producing bacteria through the combined effect of TRAIL-induced apoptosis and AHL-mediated inhibition of inflammation regulated by NF-κB signaling. This discovery unveils a previously unrecognized symbiotic link between bacteria and host immunosurveillance.

The invention provides, in various embodiments, a pharmaceutical composition comprising an effective amount of an N-acylhomoserine lactone (AHL) analog compound of formula (I):

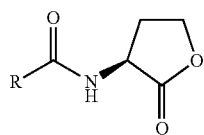

(I)

wherein R is a linear alkyl, alkenyl or alkynyl of about 9 to about 15 carbon atoms having one or more diazirenyl groups, optionally having one or more carbonyl groups at positions 4 or greater on the alkyl, alkenyl or alkynyl groups, and further optionally substituted with azido, hydroxyl, or halo; or a pharmaceutically acceptable salt thereof; and, optionally, a pharmaceutically acceptable excipient. For example, the AHL compound can be a compound is of formula (II)

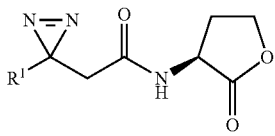

(II)

wherein $R^1$ is a linear alkyl, alkenyl or alkynyl of about 7 to 13 carbon atoms, optionally having one or more of:

(a) a diazirenyl group;
(b) one or more carbonyl groups;
(c) or, one or more independently selected azido, hydroxyl, or halo groups.

For example, the compound of formula (I) can be the (S)-enantiomer of the compound with respect to the chiral center at the position of bonding of the nitrogen atom to the lactone ring.

In various embodiments, the invention provides a method of treating a tumor in a patient, comprising administering to the patient an effective amount of an N-acylhomoserine lactone (AHL) analog compound of formula (I) as described above. Optionally, an effective amount of a tumor modulating agent such as a TRAIL polypeptide can also be administered.

In various embodiments, the invention provides a method for inducing apoptosis, arrest of cell division, or inhibition of cell proliferation, in a tumor cell, comprising contacting the cell with an effective amount of an N-acylhomoserine lactone (AHL) compound, and, optionally, an effective amount of a tumor modulating agent, such as a TRAIL polypeptide, wherein the AHL compound is of formula (I), as described above.

In various embodiments, the invention provides methods of synthesis of AHL analogs of the invention, useful for practicing methods of the invention.

In various embodiments, the invention provides a kit comprising a compound of the invention, such as compound (S)-(3-$N_2$), optionally dissolved in a pharmaceutically acceptable liquid medium, in a container, the kit optionally further comprising a tumor modulating agent, such as TRAIL, optionally dissolved in a pharmaceutically acceptable liquid medium, in a second container; further optionally comprising dosing or storage information, or both.

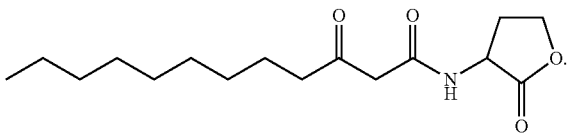 [SMILES: CCCCCCCCCC(=O)CC(=O)NC1CCOC1=O]

FIG. 2: C12 Induces the UPR through modulation of the sphingolipid medabolism. (A and B) RT-PCR assays of XBP1 in total RNA prepared from the macrophages treated with C12, Tm or Tg in the presence or absence of CHX (A) or D-MAPP (B) as indicated. (C) Western blot analysis shows the effect of D-MAPP on (C12)-induced phosphorylation of eIF2α (p-eIF2α) and p38 (p-p38); Western blot for actin is a loading control. (D) Macrophages were stimulated with LPS in the presence or absence of D-MAPP, and total protein extracts were prepared and analyzed by Western blot for p-p38 and expression of IκBα. (E) RT-PCR assay (top panel) or Western blot (bottom panel) monitors the levels of XBP1 or eIF2α or p-p38 in samples prepared from macrophages after treatment with (C12), sphingosine (Sph) or dimethylsphingosine (DMS). (F) TLC assay monitors $^3$H-Sph metabolism in macrophages treated with DMSO (Vehicle) or C12 as indicated. Location of standard sphingolpids is indicated on the left. Cer, ceramide; Sph, sphingosine; S1P, sphingosine 1-phosphate; SM, sphingomyelin.

FIG. 3: Sensitivity of cancerous and non-cancerous cells to apoptosis induced by TNF, C12 or a combination of C12 and TNF. Cells were incubated with TNF, (C12) or a combination of TNF and (C12) as indicated, and the cleavage of PARP (an apoptotic marker) was determined by Western blot. (A and B) Breast cancer MCF-7 cells transfected with control vector (Vector) and vector expressing Bcl-2 or CLARP. (C) HeLa cell line. (D) Normal human bronchial epithelial cells (NHBE).

FIG. 4: C12 sensitizes lung cancer cell line A549 to TRAIL. (A) Viability of cells was examined after 24-hour incubation in media containing TRAIL (50 ng/ml), compound (C12) (1 μM), compound (C12R) (25 μM) or the indicated combination of TRAIL (T) with (C12) or (C12R). The chemical structures of (C12) and its stereoisomer (C12R) are shown on the right. (B) Viability of cells was examined after 24-hour incubation in media containing TRAIL (50 ng/ml) and the indicated doses of C12. Viable cells remaining after the treatment were determined as a function of mitochondrial activity of living cells according to XTT-based toxicology assay kit (Sigma) and are shown as a percentage of viable untreated cells.

Figure 5:
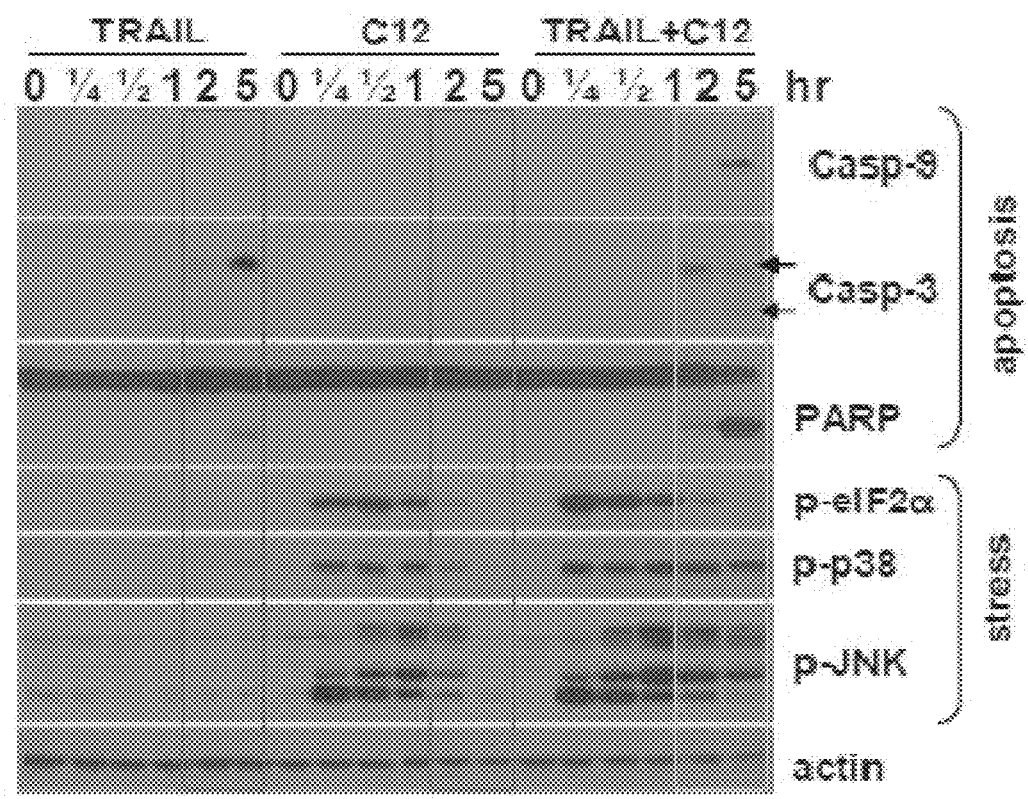

FIG. 5: C12 sensitizes lung cancer cell line A549 to TRAIL-induced apoptosis. Cells were treated with TRAIL, (C12) or a combination of TRAIL and (C12) for indicated period of time, and cellular extracts were examined by Western blot analysis for the apoptotic markers (the cleaved form of caspase-9, caspase-3 or PARP), the stress responses (the phosphorylated forms of eIF2α, p38 or JNK), and actin (a loading control).

Figure 6A:
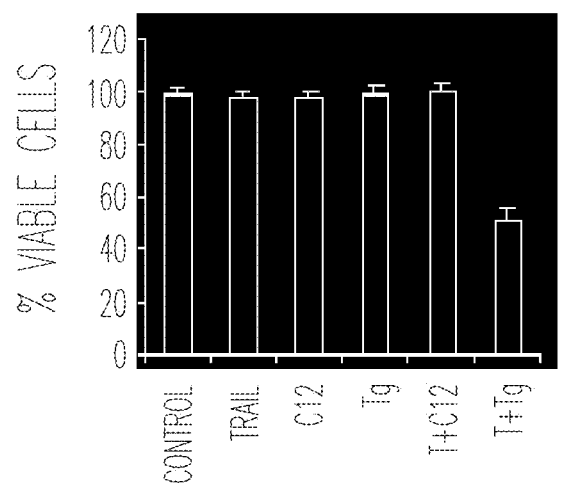
Figure 6B:
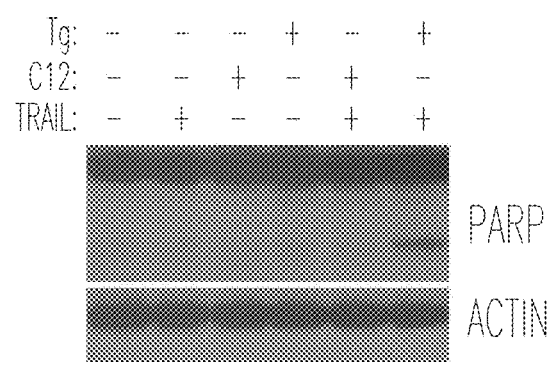

FIG. 6: Primary human B cells are resistant to TRAIL in the presence of C12. (A) Cells were treated by TRAIL (T), (C12), thapsigargin (Tg) or a combination as indicated. Viable cells remaining after a 24-hours treatment were determined as a function of mitochondrial activity of living cells according to XTT-based toxicology assay kit (Sigma) and are shown as a percentage of viable untreated cells. (B) Cells were treated 6 hr by TRAIL, (C12), thapsigargin (Tg) or a combination as indicated. The cellular extracts were examined by Western blot for the cleavage of PARP as an apoptotic marker or for actin as a loading control.

Figure 7:
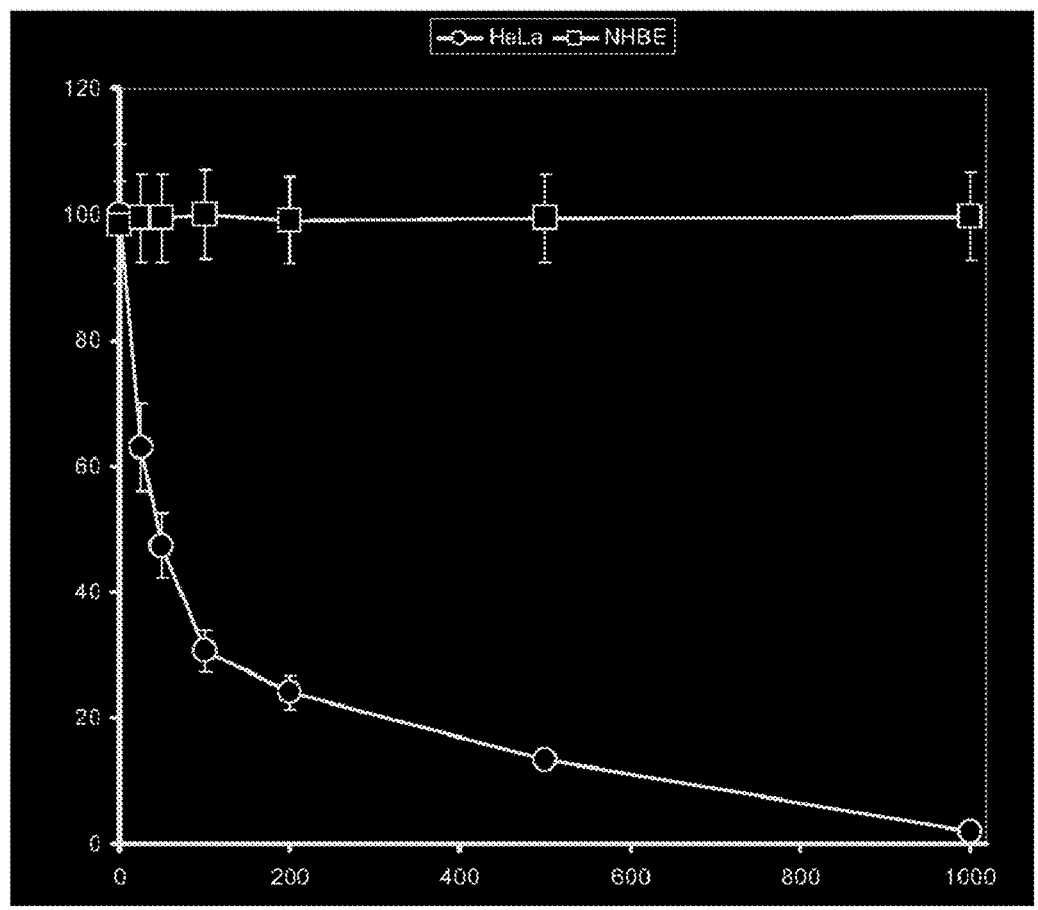

FIG. 7: Sensitivity of cancerous and non-cancerous cells to a combination of TRAIL and (C12). Normal human bronchial epithelial (NHBE) and cancerous human HeLa cells were incubated with TRAIL and indicated doses of (C12), and cell viability relative to untreated control was determined by XTT assay.

FIG. 8: Safety and pro-apoptotic activity of (C12). Cells were incubated with TRAIL, (C12), bormetazomid (Bor) or a combination of TRAIL and (C12) or Bor as indicated, and cell viability (top panels) or the cleavage of PARP (bottom panels) was determined. (A) Lung cancer cell line A549. (B) Primary human hepatocytes from normal donor.

Figure 9A:
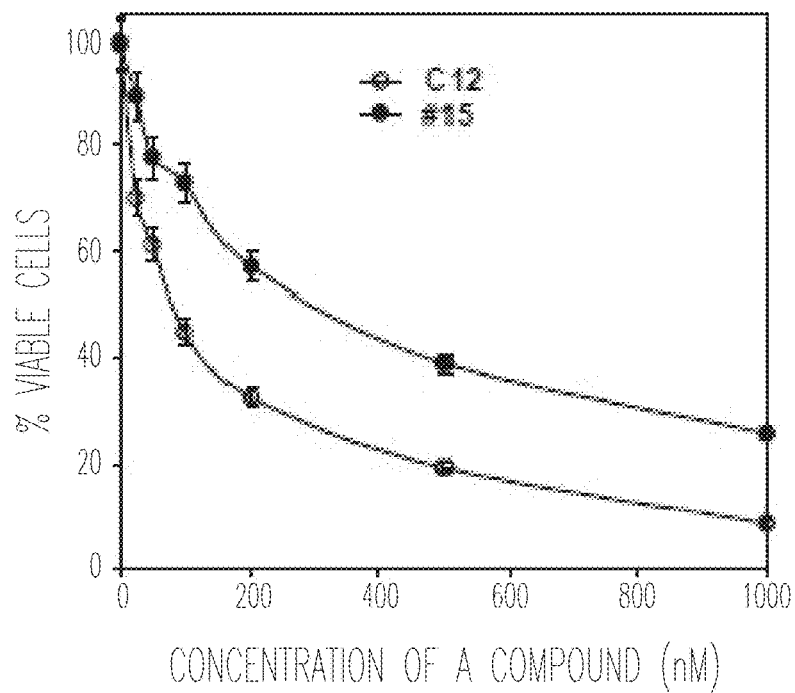
Figure 9B:
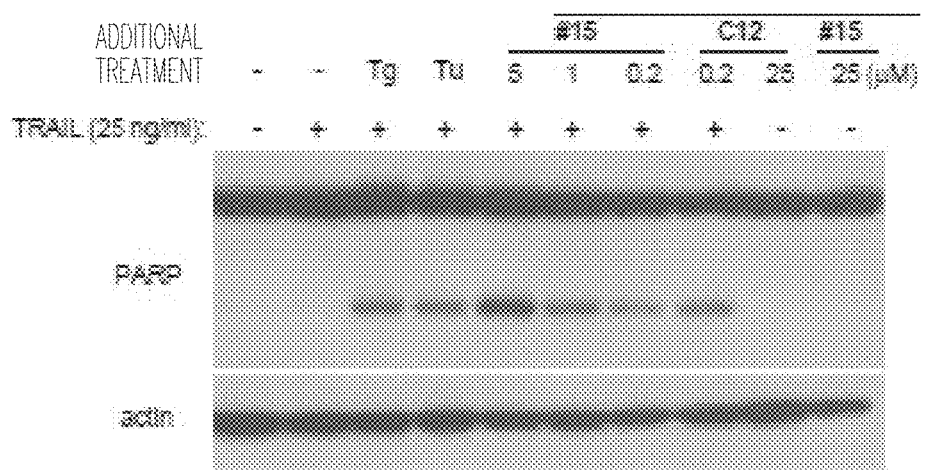

FIG. 9: Comparison of (C12)-mediated and compound #15-mediated effects on sensitivity of cancerous cells to TRAIL. (A) Viability of A549 cells was examined after 24-hour incubation in media containing TRAIL (25 ng/ml) and the indicated doses of (C12) or its analog (#15) (see Table 1). (B) A549 cells were treated by TRAIL, tunicamycin (Tu), thapsigargin (Tg), compound #15, (C12) or a combination as indicated. The cellular extracts were examined by Western blot for the cleavage of PARP as an apoptotic marker or for actin as a loading control.

Figure 10A:
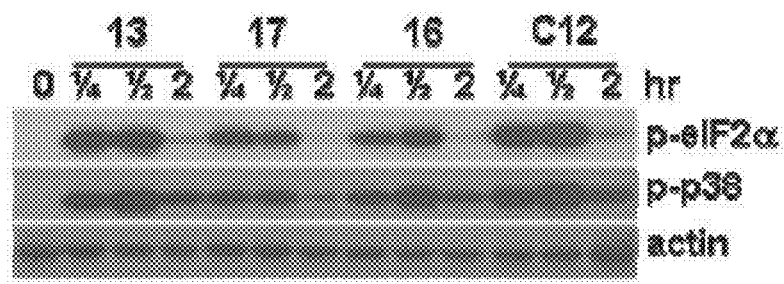
Figure 10B:
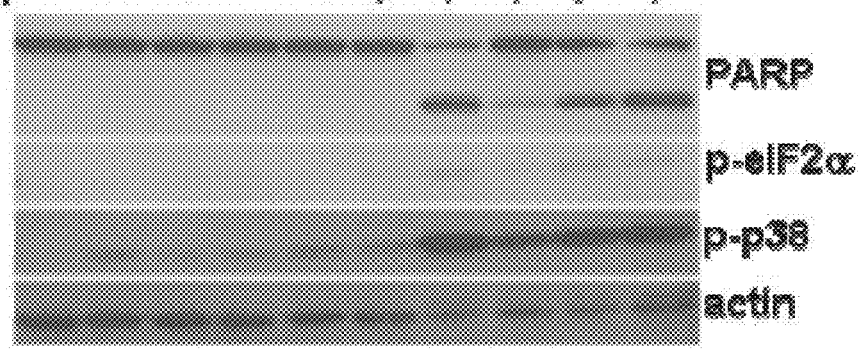

FIG. 10: Biological activity of the analogs. (A) Lung cancer A549 cells were treated by (C12) or its analogs (compound 13, 16 and 17, see Table 1) as indicated, and the cellular extracts were examined by Western blot for the phosphorylated forms of eIF2α or p38 and actin as a loading control. (B) A549 cells were treated by TRAIL, compound, (C12) or a combination as indicated, and the cellular extracts were prepared (6-hour treatment) and examined by Western blot for the cleavage of PARP as an apoptotic marker as well as indicated in (A).

FIG. 11. (C12)-producing bacteria or (C12) promote cytokine-mediated apoptosis in cancer cells. a) Chemical structures of AHLs examined in this study. b) Lung cancer cells were incubated with or without P. aeruginosa (Bac) wild type (wt) or a lasI mutant strain (ΔlasI) in the presence or absence of TNF or TRAIL as indicated. After 2 h, cell lysates were prepared and analyzed by immunoblotting with antibodies specific for PARP or actin as a loading control. c) Lung cells were untreated (Mock) or treated with TNF or TRAIL in the presence of the indicated doses of (C12) for 6 h; cell samples were analyzed as in b). d) Comparison of lung cell responsiveness to TRAIL, (C12) or their combination. Western blot analysis of PARP, IκBα, the phosphorylated form of p38 (p-p38) and actin in cellular extracts prepared after treatment with stimuli as indicated.

FIG. 12. (C12) promotes the TRAIL-mediated killing of cancer cells. a), c) Western blot analysis of PARP cleavage in cancer or normal cells treated for 3 h with TRAIL, (C12) or a combination of both, as indicated. b), d) XTT-based assay monitoring the viability of cancer and normal cells grown for 18 h in media containing TRAIL and the indicated doses of (C12). Cell survival was ~100% in control samples (untreated cells) as well as in samples incubated with TRAIL alone or the same doses of (C12) without TRAIL.

FIG. 13. AHL-mediated inhibition of inflammation-induced NF-κB signaling is sufficient for rendering tumors susceptible to TRAIL-induced apoptosis. a) Western blot analysis of PARP cleavage in cancer cells stimulated for 3 h with TRAIL or its combination with different AHLs as indicated. b) Western blot analysis of PARP cleavage as well as phosphorylated forms of eIF2α and p38 in extracts from bone marrow-derived macrophages (BMDM) stimulated with (C12) or (3-$N_2$), i.e., (S)-(3-$N_2$), as indicated. c) Western blot analysis of PARP cleavage and temporal profiles of IκBα expression in BMDM extracts prepared after treatment with LPS or its combination with (C12) or (3-$N_2$) . . . d) Inhibitory effect of (C12) and its derivatives on LPS-induced TNF production in BMDM. e) Lung cancer cells were exposed to (3-$N_2$) (10 μM), TRAIL (0.5 ng/ml), TNF (20 ng/ml) or their combinations as indicated. After 2 h, cell lysates were prepared and analyzed by Western blot for PARP cleavage, IκBα and actin.

DETAILED DESCRIPTION

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C—CH$_3$), —C≡C—CH$_2$CH$_3$), —CH$_2$C≡CH, —CH$_2$C≡C—CH$_3$), and —CH$_2$C≡C—CH$_2$CH$_3$) among others.

When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (═O) group, the oxygen substituent is termed an "oxo" group. When it is stated herein that an alkyl, alkenyl, or alkynyl group comprises an carbonyl group, what is referred to is an alkyl, alkenyl, or alkynyl chain respectively wherein a carbon atom of the chain is double bonded to an oxygen atom, e.g., of formula

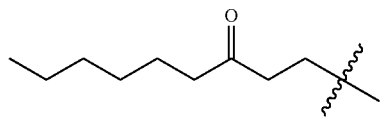 [SMILES: *CCC(=O)CCCCCC]

wherein a wavy line indicates a point of attachment. The carbonyl group can also be bonded any other carbon atom of the alkyl, alkenyl, or alkynyl.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "hydroxyl" group is a carbon-bonded OH group.

The term "azido" refers to an $N_3$ group, of formula

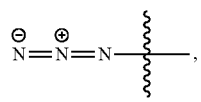

wherein a wavy line indicates a point of attachment.

An "diazirenyl" group as the term is used herein refers to a three-membered ring including one carbon atom and two nitrogen atoms, wherein the two nitrogen atoms are double bonded to each other and each nitrogen atom is single bonded to the carbon atom, e.g., of structure:

wherein the tetrahedral carbon atom can be bonded to two further substituents. When it is stated herein that an alkyl, alkenyl, or alkynyl group comprises a diazirenyl group, what is referred to is an alkyl, alkenyl, or alkynyl chain respectively wherein a saturated carbon atom of the chain is the carbon atom bonded to each of the two nitrogen atoms. For example, a C10 alkyl group comprising a diazirenyl group can be of formula

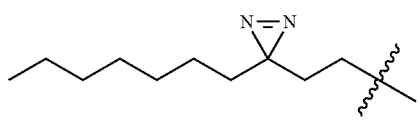 [SMILES: *CCC1(CCCCCCC)N=N1]

wherein a wavy line indicates a point of attachment. The diazirenyl group can also be bonded any other carbon atom of the alkyl, alkenyl, or alkynyl.

An "N-acylhomoserine lactone (AHL) analog" as the term is used herein can refer to a compound of formula (I)

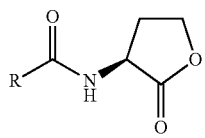

(I)

of the (S) absolute configuration as designated under the Cahn-Ingold-Prelog system, wherein group R is a linear alkyl, alkenyl or alkynyl chain of about 9 to about 15 carbon atoms, which can incorporate diazirenyl groups, carbonyl groups, or both, and can be further substituted with groups as defined above.

An example of a compound of formula (I) is compound (3-$N_2$)

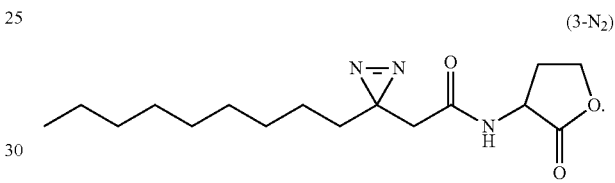

(3-$N_2$)

The diazirene is bonded to the 3-carbon of the acyl chain, and this nomenclature is used throughout.

As is apparent, a chiral center is present at the position of butyrolactone ring substitution. Accordingly, the compound can be of either configuration, but the (S)-(3-$N_2$) compound is preferred, which can variously be displayed as

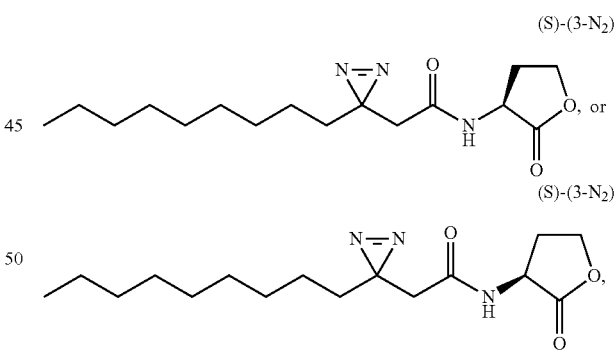

(S)-(3-$N_2$)

(S)-(3-$N_2$)

without any change in the meaning of the structure; both represent the (S)-enantiomer.

There are naturally occurring AHL compounds

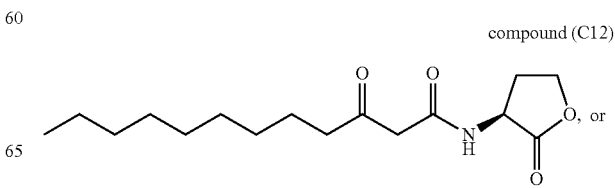

compound (C12)

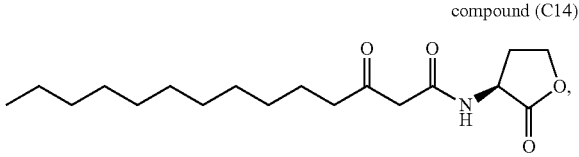

compound (C14)

which can be used in various embodiments of methods of the invention for inducing apoptosis in a tumor cell, or in treating a patient with cancer.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydroiodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents that do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is nonvolatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

DETAILED DESCRIPTION

We examined the Gram-negative bacteria *Pseudomonas aeruginosa*, an opportunistic pathogen that is only able to promote infection in hosts with defective immune system functions (Smith, R. S. and Iglewski, B. H. (2003) *Pseudomonas aeruginosa* quorum sensing as a potential antimicrobial target. *J Clin Invest* 112, 1460-5). As compound (C12)

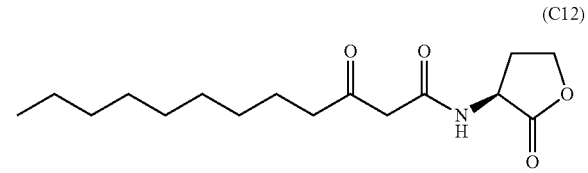 [SMILES: CCCCCCCCCC(=O)CC(=O)N[C@H]1CCOC1=O]

(C12)

is a signaling molecule produced in abundance by this bacteria, we examined whether wild type *P. aeruginosa* or a mutant strain lacking lasI, the gene responsible for the synthesis of compound (C12), could render lung cancer cells susceptible to TNF- or TRAIL-induced cleavage of poly (ADP-ribose) polymerase (PARP), an indicative characteristic of apoptosis. Excitingly, PARP cleavage was only detected when cells received a combination of TRAIL and wild type bacteria (FIG. 11b), suggesting that compound (C12) was required for TRAIL-induced apoptosis in cancer cells. Notably, similar results were observed when other AHL-producing bacteria were added to cytokine-stimulated cells, while bacteria that do not possess AHL synthases had no effect. Furthermore, titration experiments confirmed that the direct addition of C12 or several naturally occurring AHL analogues resulted in a strong pro-apoptotic response to TNF or TRAIL, and in agreement with our bacterial experiments, the cells were more sensitive to TRAIL (FIG. 11c).

Since activation of NF-κB signaling inhibits apoptosis, the observed difference in the pro-apoptotic effects of TNF and TRAIL might be linked to the distinct ability of these cytokines to modulate NF-κB activity. Consistent with this interpretation, Western blot analysis for the degradation and re-synthesis of IκBα, an indicative biochemical marker of NF-κB signaling, revealed a robust activation of NF-κB signaling in response to TNF but not to TRAIL. Although no modulation of NF-κB or apoptotic signaling was induced in response to TRAIL or compound (C12), substantial changes in the levels of IκBα were matched with PARP cleavage in lung cancer cells stimulated with a combination of compound (C12) and TRAIL (FIG. 11d). Interestingly, we also observed that the combined action of TRAIL and compound (C12) resulted in a prolonged activation of the mitogen-activated protein kinase (MAPK) p38 as determined by Western blot analysis for the phosphorylated form of p38 (FIG. 11d; p-p38). These findings suggest that compound (C12) enhances TRAIL's ability to execute apoptosis in cancer cells through modulation of NF-κB, p38 or both signaling processes.

Despite the expression of TRAIL receptors, normal cells are resistant to TRAIL-induced apoptosis. Similar to non-transformed cells, many malignant cells are not sensitive or only partially sensitive to the pro-apoptotic action of TRAIL. Therefore, in order to assess the selectivity of compound (C12) as a modulator of TRAIL-dependent tumor immunosurveillance, we compared the sensitivity of several cancer cell lines and normal cells to TRAIL and compound (C12). Consistent with our previous observations, substantial induction of PARP cleavage was observed in lung, colon and breast cancer cells stimulated with a combination of compound (C12) and TRAIL. In contrast, human hepatocytes from normal donors as well as other primary cells from normal tissues were resistant to the same treatment (FIGS. 12a and 12c). Importantly, longer treatment of cancer cells with TRAIL plus compound (C12) significantly decreased their viability although no effect on the survival of normal cells was noted (FIGS. 12b and 12d).

While these data demonstrate a therapeutic potential of compound (C12) as an enhancer of TRAIL-dependent anti-cancer activity, questions concerning (C12)-mediated pro-apoptotic effects on immune cells, such as primary macrophages, were still required to be addressed. Considering the potential inherent pharmacokinetic liabilities associated with C12, a small series of compound (C12) analogues was tested against bone marrow-derived macrophages and TRAIL-treated lung cancer cells. From these studies, an AHL lacking the 3-oxo moiety was found to be completely inactive in both assays; however, a 3-diazirine-containing derivative of compound (C12) termed compound (3-N$_2$)

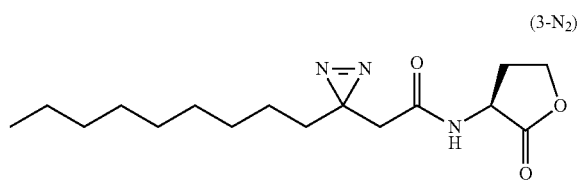 [SMILES: CCCCCCCCCC1(CC(=O)N[C@H]2CCOC2=O)N=N1]

Figure 13A:
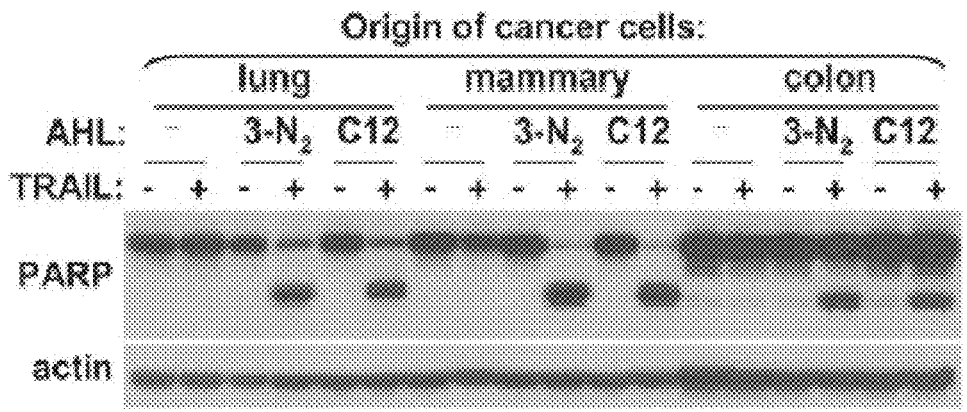
Figure 13B:
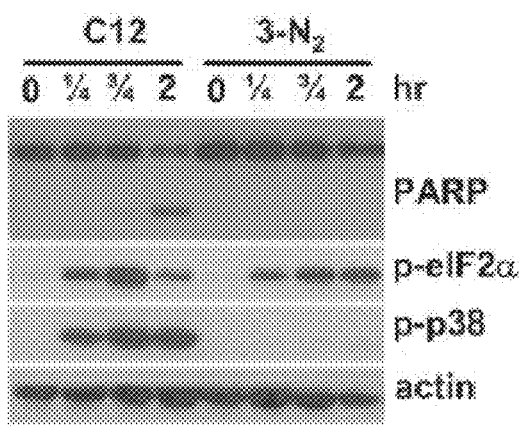

(3-N$_2$)

the (S)-enantiomer of which is referred to, wherein a diazirine ring (i.e., containing a double bond between the two nitrogen atoms) replaces the carbonyl group of compound (C12); (see the Examples, below, for structure, synthesis and characterization data) was found to be nontoxic to macrophages, yet exhibited toxicity against TRAIL-treated cancer cells in a manner similar to the parental molecule. Moreover, we also observed a comparable effect of compound (C12) and compound (3-N$_2$) on TRAIL-induced PARP cleavage in TRAIL resistant cancer cells (FIG. 13a).

To better define the structure-activity relationship between AHL-mediated effects on the pro-apoptotic action of TRAIL and the agonistic potential of (C12) or compound (3-N$_2$), the responses of macrophages to these compounds were examined by Western blot analysis for PARP cleavage, activation of p38, and the phosphorylation of the eukaryotic translation initiation factor 2α (eIF2α), a distinct feature of mammalian cell activation in response to C12 and its 3-oxo-analogues. A comparison of the agonistic activities of compound (C12) and compound (3-N$_2$) revealed that both compounds induced eIF2α phosphorylation in a similar fashion; however, compound (3-N$_2$) did not induce p38 phosphorylation and PARP cleavage (FIG. 13b), suggesting that activation of the p38 pathway promotes AHL-induced apoptosis in addition to stimulating phagocytic activity, as previously disclosed.

Figure 13C:
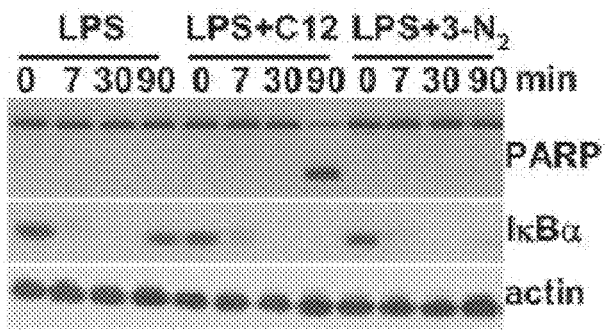
Figure 13D:
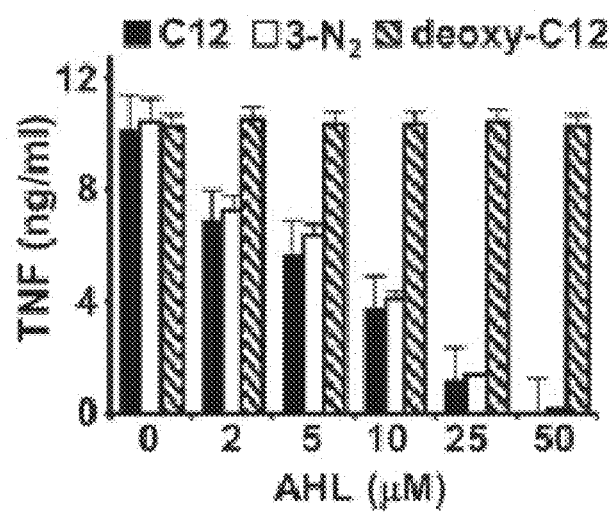

Besides its agonistic activities, compound (C12) also inhibits inflammatory responses to TNF, LPS and other TLR ligands in a wide variety of cell types. In macrophages, the anti-inflammatory activity of C12 interferes with the inducible expression of NF-κB target genes, such as IκBα and TNF. Our results also suggest that AHL-mediated disruption of IκBα-dependent NF-κB signaling renders cancer cells susceptible to TNF- and TRAIL-induced apoptosis (see FIG. 11d). Therefore, to examine whether compound (3-N$_2$) affects stimulus-induced NF-κB signaling, we compared the dynamics of IκBα expression in macrophages activated by LPS or its combination with compound (C12) or compound (3-N$_2$). Curiously, although the expected pro-apoptotic cleavage of PARP was observed in the presence of compound (C12) but not compound (3-N$_2$), both compounds were equally effective in blocking LPS-induced re-synthesis of IκBα (FIG. 13c). Moreover, similarity between the anti-inflammatory activities of compound (C12) and compound (3-N$_2$) were also evident from comparison of their inhibitory effects on LPS-induced production of TNF (FIG. 13d). These experiments indicate that compound (3-N$_2$) is non-toxic to resting or inflammation-activated macrophages; however, it retains the ability of C12 to modulate LPS-induced NF-κB signaling.

Figure 13E:
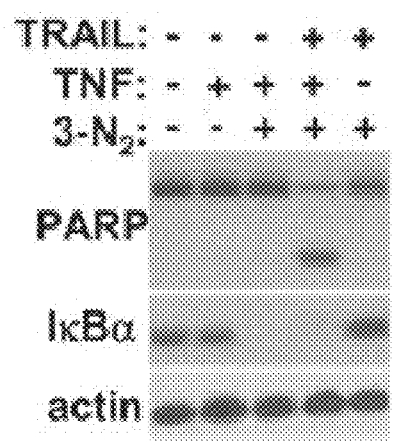

TNF is a key inflammatory mediator responsible for LPS-induced tumor growth, and the growth-promoting activity of TNF is dependent on NF-κB activation. Most importantly, experiments using a mouse model of LPS-induced tumor growth suggest that inhibition of TNF-mediated NF-κB signaling in cancer cells converts inflammation-induced tumor growth to inflammation-induced tumor regression mediated by endogenous TRAIL. To address whether an AHL is able to enhance the anti-cancer activity of TRAIL in inflammation-activated cancer cells, we examined the effect of a suboptimal concentration of TRAIL on PARP cleavage in cancer cells treated with a combination of TNF and compound (3-N$_2$). Western blot analysis revealed that TRAIL-dependent PARP cleavage was manifested in cancer cells stimulated with TNF in the presence of compound (3-N$_2$), and significantly, the TRAIL-mediated apoptotic response coincided with disruption of TNF-induced NF-κB signaling (FIG. 13e).

In sum, the identification of compound (C12) and its analogues such as compound (3-N$_2$) as "TRAIL-enhancers" and the ability of these compounds to inhibit pro-inflammatory responses through modulation of NF-κB signaling provide a proof-of-principle application for the selective killing of cancer cells. Notably, the synergistic effects of compound (3-N$_2$) on TRAIL-induced apoptosis in cancer cells were comparable with those for an anti-cancer agent bortezomib; however, in contrast to bortezomib, compound (3-N$_2$) alone or in combination with TRAIL was non-toxic to human hepatocytes derived from tissues of normal donors. A linkage of cancer and inflammation suggests a substantial benefit can be gained from using anti-inflammatory agents, such as inhibitors of NF-κB, in cancer therapy and prevention.

Accordingly, in various embodiments, the invention provides a pharmaceutical composition comprising an effective amount of an N-acylhomoserine lactone (AHL) analog compound of formula (I):

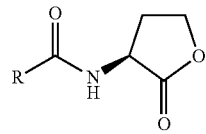
(I)

wherein R is a linear alkyl, alkenyl or alkynyl of about 9 to about 15 carbon atoms having one or more diazirenyl groups bonded thereto, optionally having one or more carbonyl groups at positions 4 or greater on the alkyl, alkenyl or alkynyl groups, and further optionally substituted with azido, hydroxyl, or halo; or a pharmaceutically acceptable salt thereof; and, optionally, a pharmaceutically acceptable excipient.

In reference to the statement about optionally having one or more carbonyl groups at positions 4 or greater on the alkyl, alkenyl or alkynyl groups, the position number (e.g., 4) refers to the carbon number of the acyl chain to which the oxygen atom is bonded (e.g., at position 4 of the acyl chain). The acyl chain forms an amide bond with the homoserine lactone amino group to provide the AHL compound.

For example, the AHL compound can be of formula (II)

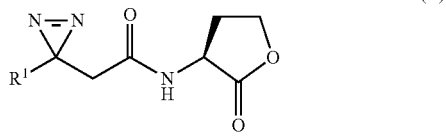
(II)

wherein $R^1$ is a linear alkyl, alkenyl or alkynyl of about 7 to 13 carbon atoms, optionally having one or more of:
(d) a diazirenyl group;
(e) one or more carbonyl groups; or
(f) one or more independently selected azido, hydroxyl, or halo groups.

In various embodiments, a pharmaceutical composition of the invention can further comprising a tumor modulating agent that is a TRAIL polypeptide.

More specifically, the N-acylhomoserine lactone (AHL) analog is selected from the group consisting of:

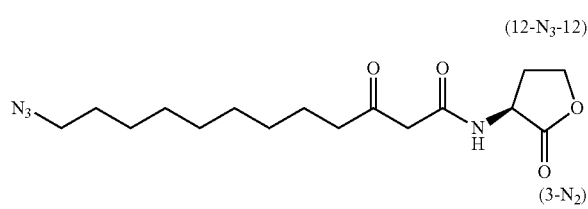
(12-N₃-12)

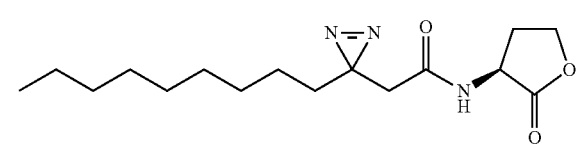
(3-N₂)

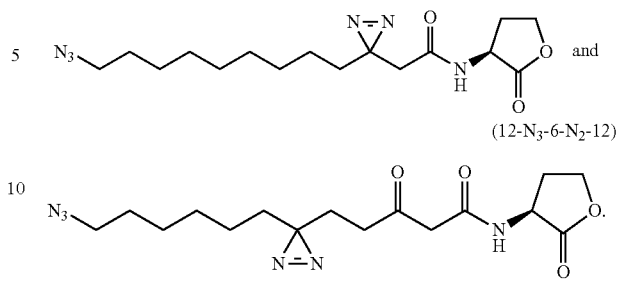
(12-N₃-3N2)
and
(12-N₃-6-N₂-12)

In various embodiments, the invention provides a method of treating a tumor in a patient, comprising administering to the patient an effective amount of an N-acylhomoserine lactone (AHL) analog compound of formula (I)

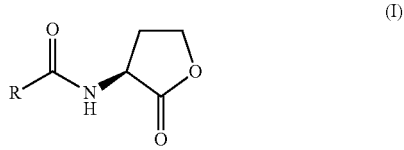
(I)

wherein R is a linear alkyl, alkenyl or alkynyl of about 9 to about 15 carbon atoms having one or more diazirenyl groups, optionally having one or more carbonyl groups, and further optionally substituted with azido, hydroxyl, or halo; or a pharmaceutically acceptable salt; and optionally, a pharmaceutically acceptable excipient. For instance, the compound can be a compound of formula (II)

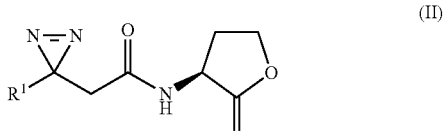
(II)

wherein $R^1$ is a linear alkyl, alkenyl or alkynyl of about 7 to 13 carbon atoms, optionally having one or more of:
(a) a diazirenyl group;
(b) one or more carbonyl groups; or
(c) one or more independently selected azido, hydroxyl, or halo groups.

The method of the invention can further comprise administering an effective amount of a tumor modulating agent that is a TRAIL polypeptide. More specifically the N-acylhomoserine lactone (AHL) analog can be selected from the group consisting of:

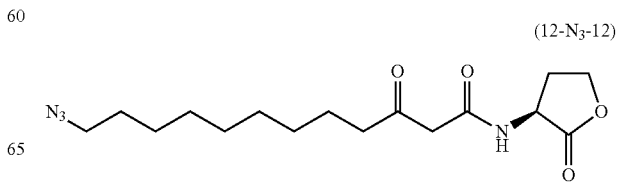
(12-N₃-12)

-continued

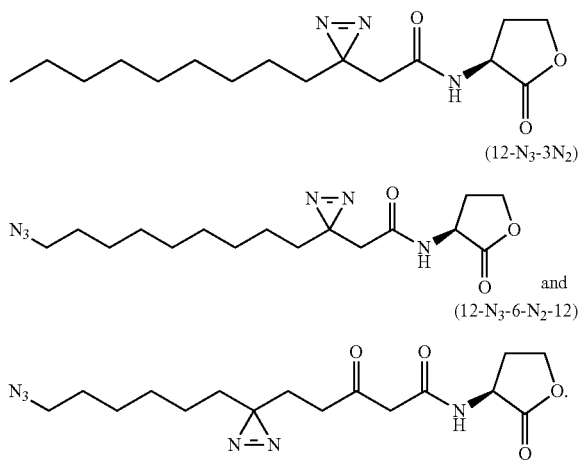

For example, the tumor that can be treated according to a method of the invention can be selected from the group consisting of lung, cervical, breast, and brain tumors.

The invention provides, in various embodiments, a method for inducing apoptosis, arrest of cell division, or inhibition of cell proliferation, in a tumor cell, comprising contacting the cell with an effective amount of an N-acylhomoserine lactone (AHL) compound, and an effective amount of a TRAIL, wherein the AHL compound is of formula (I):

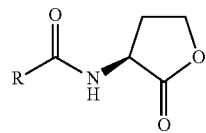

wherein R is a linear alkyl, alkenyl or alkynyl of about 9 to about 15 carbon atoms having one or more diazirenyl groups, optionally having one or more carbonyl groups, and further optionally substituted with azido, hydroxyl, or halo. For example, in various embodiments, the AHL analog in the effective amount is an activator of the unfolded protein response (UPR), of endoplasmic reticulum swelling (ERS), or both, in the tumor cell.

More specifically, for practice of a method of the invention, the AHL compound is a compound of formula (II)

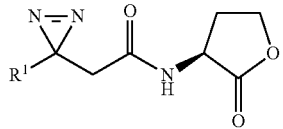

wherein $R^1$ is a linear alkyl, alkenyl or alkynyl of about 7 to 13 carbon atoms, optionally having one or more of:
(a) a diazirenyl group;
(b) one or more carbonyl groups; and
(c) one or more independently selected azido, hydroxyl, or halo groups.

More specifically, the N-acylhomoserine lactone (AHL) analog can be selected from the group consisting of:

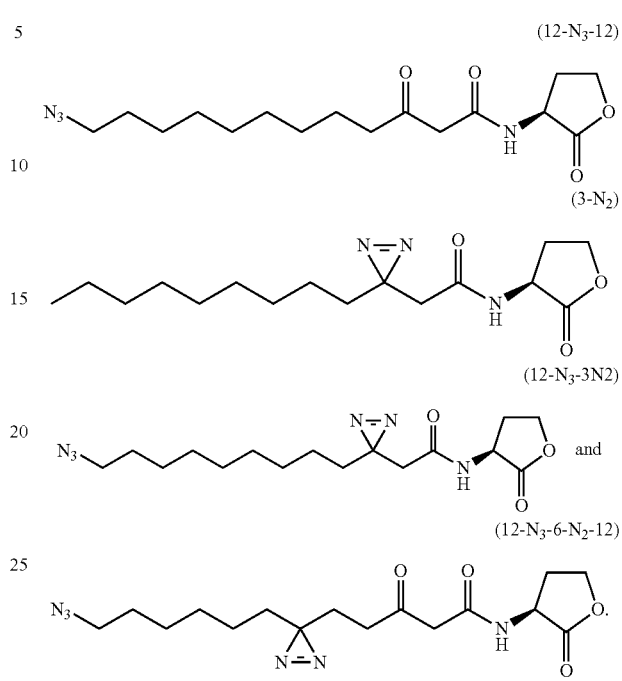

The tumor cell can be from a tumor selected from the group consisting of lung, cervical, breast, and brain tumors.

The present invention further provides, in various embodiments, a compound of formula (I):

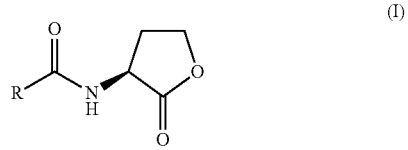

wherein R is a linear alkyl, alkenyl or alkynyl of about 9 to about 15 carbon atoms having one or more diazirenyl groups, optionally having one or more carbonyl groups at positions 4 or greater on the alkyl, alkenyl or alkynyl groups, and further optionally substituted with azido, hydroxyl, or halo; or, a pharmaceutically acceptable salt thereof. For example, the compound can be a compound of formula (II)

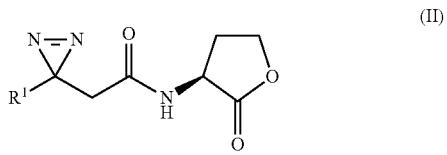

wherein $R^1$ is a linear alkyl, alkenyl or alkynyl of about 7 to 13 carbon atoms, optionally having one or more of:
(a) a diazirenyl group;
(b) one or more carbonyl groups; or
(c) one or more independently selected azido, hydroxyl, or halo groups.

The compound of formula (I) as described above can be provided in a pharmaceutical combination with a tumor modulating agent that is a TRAIL polypeptide. For example, the N-acylhomoserine lactone (AHL) analog of the invention can be selected from the group consisting of:

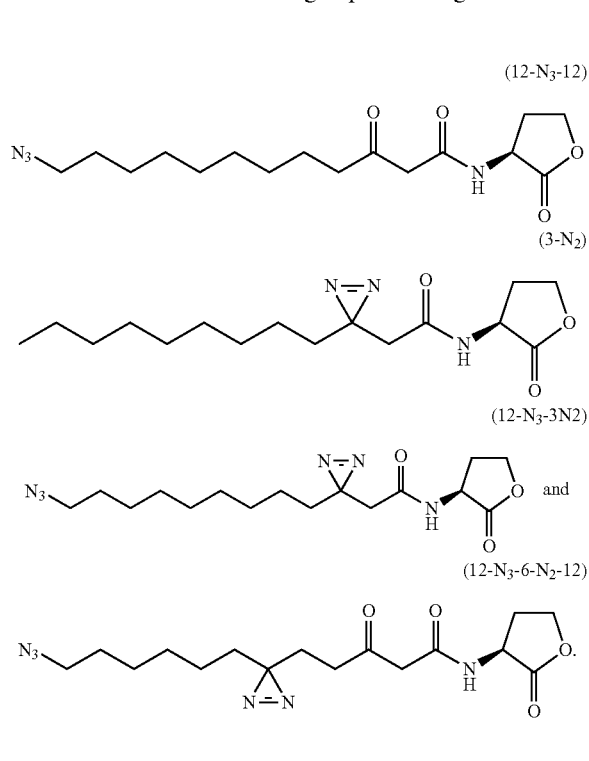

In various embodiments, the invention provides a method of inducing apoptosis in a cell comprising contacting the cell with an effective amount of the N-acylhomoserine lactone (AHL) analog as described above, provided the AHL analog is not of formulas

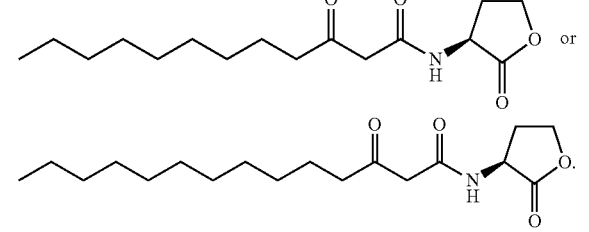

Optionally, the method of inducing apoptosis further comprises administering an effective amount of a tumor modulating agent, such as TRAIL. The method of inducing apoptosis can be selective for a cancer cell with respect to a normal cell.

In various embodiments, the invention provides a method of treating a tumor in a patient, comprising administering to the patient an effective amount of an N-acylhomoserine lactone (AHL) analog, plus an effective amount of a tumor modulating agent, such as TRAIL. In various embodiments, the AHL analog is not of formulas

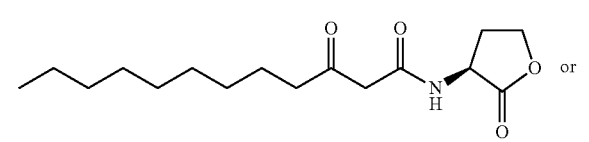

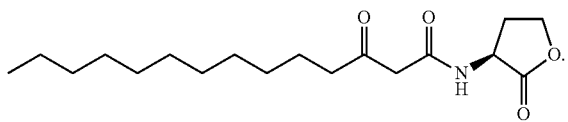

In various embodiments, the method of treating a tumor can provide selective killing of cells of the tumor in the presence of normal cells of the patient's body.

The compound of formula (I) can be a compound of formula (3-N$_2$)

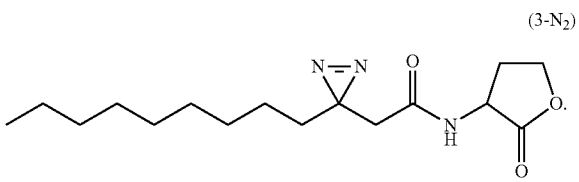 [SMILES: CCCCCCCCCC1(CC(=O)NC2CCOC2=O)N=N1]

For example, the compound of formula (I) can be the (S)-enantiomer of a compound of formula (3-N$_2$)

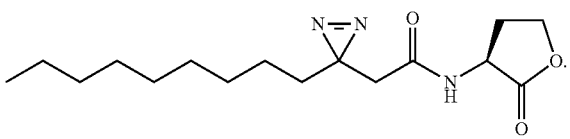 [SMILES: CCCCCCCCCC1(CC(=O)N[C@H]2CCOC2=O)N=N1]

In various embodiments, the invention provides a compound of formula (I)

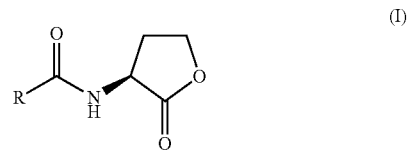

wherein R is a linear alkyl, alkenyl or alkynyl of about 9 to about 15 carbon atoms, comprising one or more diazirenyl group, optionally further comprising one or more a carbonyl group, and further optionally substituted with azido, hydroxyl, or halo, or a pharmaceutically acceptable salt thereof, provided that the compound is not

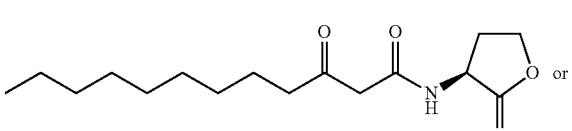

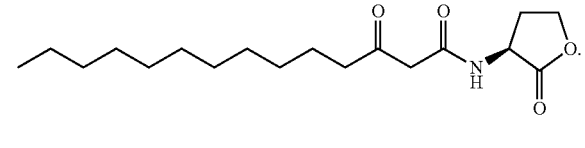

In various embodiments, the invention provides a compound of formula (3-N₂)

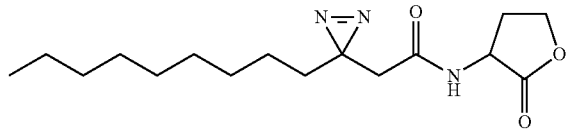 [SMILES: CCCCCCCCCC1(CC(=O)NC2CCOC2=O)N=N1]

wherein the diazirine ring, containing a double bond between the two nitrogen atoms, replaces the carbonyl group of the compound C12 to provide compound (3-N₂).

In various embodiments, the invention provides a pharmaceutical composition comprising a compound of the invention, and a pharmaceutically acceptable excipient.

In various embodiments, the invention provides a kit comprising a compound of the invention, optionally dissolved in a pharmaceutically acceptable liquid medium, in a container; the kit optionally further comprising a tumor modulating agent, such as TRAIL, optionally dissolved in a pharmaceutically acceptable liquid medium, in a second container; further optionally comprising dosing or storage information, or both.

More specifically, the N-acylhomoserine lactone (AHL) analog of formula (I) as disclosed and claimed herein can be any of:

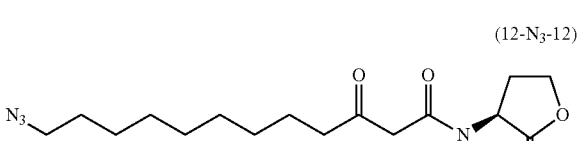
(12-N₃-12)

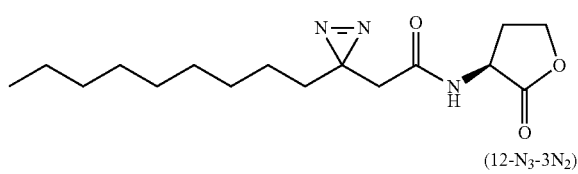
(3-N₂)

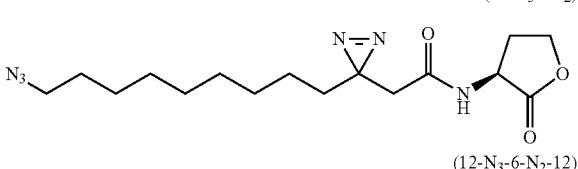
(12-N₃-3N₂)

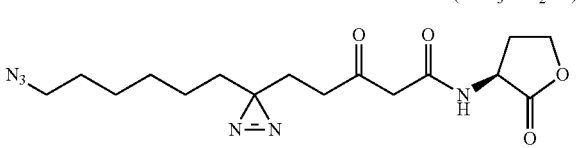
(12-N₃-6-N₂-12)

or any pharmaceutically acceptable salt thereof.

The tumor can be a lung tumor, a cervical tumor, breast cancer, brain cancer, or the like. In various embodiments, the AHL analog of formula (II) can be in an effective amount an activator of the unfolded protein response (UPR), of endoplasmic reticulum swelling (ERS), or both, in the tumor cell.

In various embodiments, the invention provides a method of inducing an unfolded protein response (UPR) in a mammalian cell comprising contacting the cell with an effective amount of an AHL or analog thereof of formula (I)

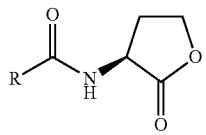

wherein R is a linear alkyl, alkenyl or alkynyl of about 9 to about 15 carbon atoms, comprising one or more diazirenyl group, optionally further comprising one or more a carbonyl group, and further optionally substituted with azido, hydroxyl, or halo, or a pharmaceutically acceptable salt thereof.

In various embodiments, the UPR thus induced can produce cell cycle arrest and/or can inhibit cell division or proliferation. Cell cycle arrest and/or inhibition of cell division or proliferation can be an effective therapy in treating neoplasms such as tumors. Accordingly, in various embodiments, the invention provides a method of treating a malcondition in a patient wherein induction of the UPR, arrest of cell division and/or inhibition of cell proliferation is medically indicated, comprising administering to the patient an effective amount of an AHL or analog thereof of formula (I)

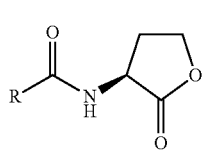

wherein R is a linear alkyl, alkenyl or alkynyl of about 9 to about 15 carbon atoms, comprising one or more diazirenyl group, optionally further comprising one or more a carbonyl group, and further optionally substituted with azido, hydroxyl, or halo, or a pharmaceutically acceptable salt thereof.

The method of treatment comprising induction of the UPR can further comprise co-administration of an effective amount or concentration of a TRAIL. For example, the malcondition can comprise cancer or a precancerous condition or tissue hyperplasia.

The invention further provides, in various embodiments, a pharmaceutical composition comprising an effective amount of an N-acylhomoserine lactone (AHL) analog from a compound of formula (I):

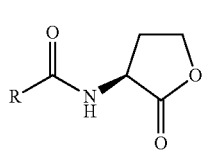

wherein R is a linear alkyl, alkenyl or alkynyl of about 9 to about 15 carbon atoms having one or more diazirenyl groups, optionally having one or more carbonyl groups at positions 4 or greater on the alkyl, alkenyl or alkynl groups, and further optionally substituted with azido, hydroxyl, or halo; and a pharmaceutically acceptable salt. For example, the compound can be a compound of formula (II)

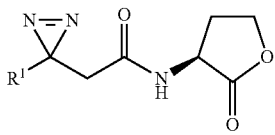

wherein R¹ is a linear alkyl, alkenyl or alkynyl of about 7 to 13 carbon atoms, optionally having:
(g) a diazirenyl group;
(h) one or more carbonyl groups; and
(i) optionally substituted with azido, hydroxyl, or halo.

In various embodiments, the invention can further provide the pharmaceutical composition as described above, further comprising a tumor modulating agent that is a TRAIL polypeptide.

More specifically, the invention provides the pharmaceutical composition as described above, wherein the N-acylhomoserine lactone (AHL) analog is selected from the group consisting of:

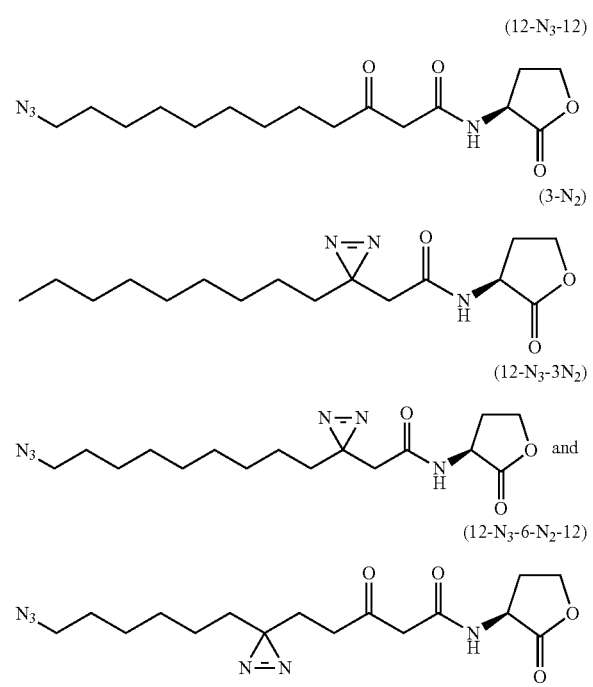

In various embodiments, the invention provides a method of treating a tumor in a patient, comprising administering to the patient an effective amount of an N-acylhomoserine lactone (AHL) analog comprising a compound of formula (I)

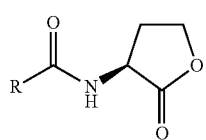

wherein R is a linear alkyl, alkenyl or alkynyl of about 9 to about 15 carbon atoms having one or more diazirenyl groups, optionally having one or more carbonyl groups, and further optionally substituted with azido, hydroxyl, or halo; and a pharmaceutically acceptable salt. For example, to practice a method of the invention, the compound can be a compound of formula (II)

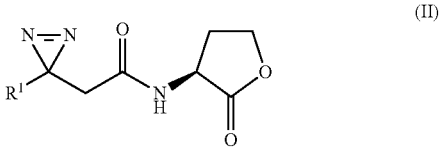

wherein R¹ is a linear alkyl, alkenyl or alkynyl of about 7 to 13 carbon atoms, optionally having:
(d) a diazirenyl group;
(e) one or more carbonyl groups; and
(f) optionally substituted with azido, hydroxyl, or halo.

For example, the method of treating a tumor in a patient as described above can further comprise administering a tumor modulating agent that is a TRAIL polypeptide. for instance, for practicing the method of treating a tumor in a patient as described above, the N-acylhomoserine lactone (AHL) analog can be selected from the group consisting of:

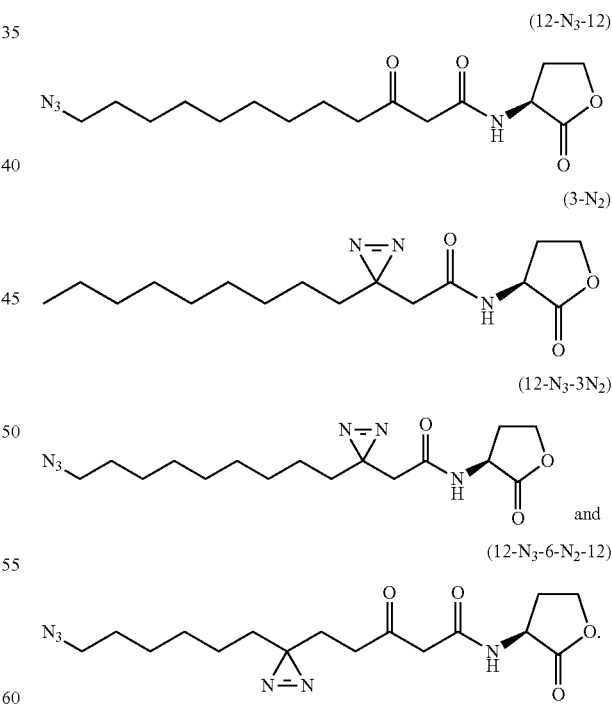

For example the tumor can be selected from the group consisting of lung, cervical, breast, and a brain tumors.

The invention further provides, in various embodiments, a compound of formula (I):

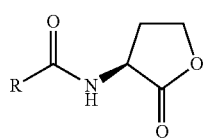

(I)

wherein R is a linear alkyl, alkenyl or alkynyl of about 9 to about 15 carbon atoms having one or more diazirenyl groups, optionally having one or more carbonyl groups at positions 4 or greater on the alkyl, alkenyl or alkynl groups, and further optionally substituted with azido, hydroxyl, or halo; and a pharmaceutically acceptable salt. For example, the compound can be a compound of formula (II)

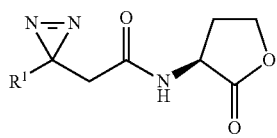

(II)

wherein $R^1$ is a linear alkyl, alkenyl or alkynyl of about 7 to 13 carbon atoms, optionally having:
(d) a diazirenyl group;
(e) one or more carbonyl groups; and
(f) optionally substituted with azido, hydroxyl, or halo.

The compound can be combined with a tumor modulating agent that is a TRAIL polypeptide. The compound of the invention can be selected from the group consisting of:

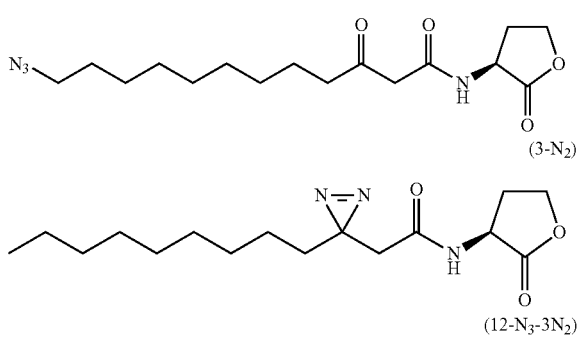

(12-N₃-12)

(3-N₂)

(12-N₃-3N₂)

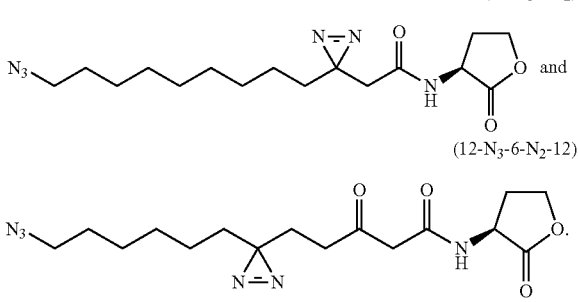

(12-N₃-6-N₂-12)

The invention further provides, in various embodiments, a method for inducing apoptosis, arrest of cell division, or inhibition of cell proliferation, in a tumor cell, comprising contacting the cell with an effective amount of an N-acylhomoserine lactone (AHL) compound, and an effective amount of a TRAIL, wherein the compound is from formula (I):

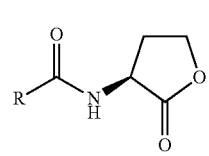

(I)

wherein R is a linear alkyl, alkenyl or alkynyl of about 9 to about 15 carbon atoms having one or more diazirenyl groups, optionally having one or more carbonyl groups, and further optionally substituted with azido, hydroxyl, or halo. More specifically, the for practice of the method for inducing apoptosis, arrest of cell division, or inhibition of cell proliferation, in a tumor cell, the AHL analog in the effective amount can be an activator of the unfolded protein response (UPR), of endoplasmic reticulum swelling (ERS), or both, in the tumor cell.

For instance, for practice of a method of the invention as described above, the compound can be a compound of formula (II)

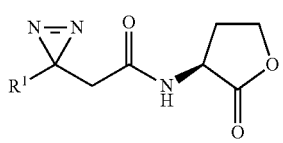

(II)

wherein $R^1$ is a linear alkyl, alkenyl or alkynyl of about 7 to 13 carbon atoms, optionally having:
(d) a diazirenyl group;
(e) one or more carbonyl groups; and
optionally substituted with azido, hydroxyl, or halo.

More specifically, for practice of the method for inducing apoptosis, arrest of cell division, or inhibition of cell proliferation, in a tumor cell, the N-acylhomoserine lactone (AHL) analog can be selected from the group consisting of:

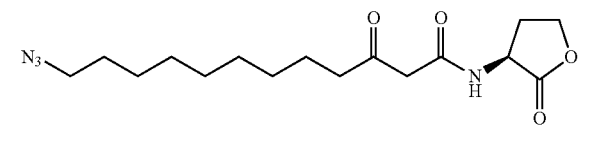

(12-N₃-12)

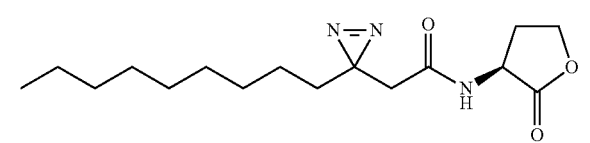

(3-N₂)

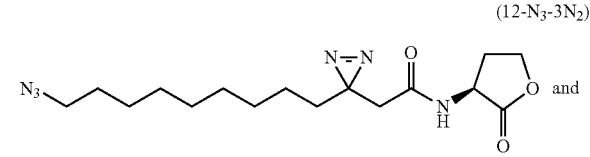

(12-N₃-3N₂)

-continued (12-N₃-6-N₂-12)

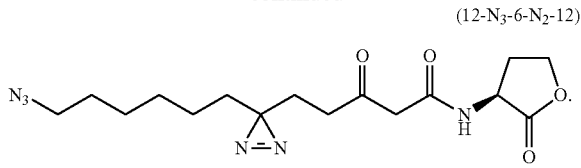

In various embodiments, the invention provides a kit comprising a AHL analog, or an compound of the invention, optionally dissolved in a pharmaceutically acceptable liquid medium, in a container; the kit optionally further comprising a tumor modulating agent, optionally dissolved in a pharmaceutically acceptable liquid medium, in a second container; further optionally comprising dosing or storage information, or both.

Biological Studies

Previous work by the inventors here have shown that bacterial N-(3-oxo-acyl) homoserine lactones (AHLs) transiently induce distention of the ER and appearance of a biochemical marker of the UPR, such as phosphorylation of eukaryotic translation initiation factor 2α (eIF2α), suggesting roles of AHLs in the UPR (V. Kravchenko, et al., *J Biol Chem* 2006, 281(39), 28822-30). Since the inositol-requiring protein 1 (IRE1)-mediated splicing of the mRNA encoding the transcription factor XBP1 (X-box binding protein) is an evolutionary conserved signature of the UPR (Schroder, M., et al, *Ann Rev Biochem* 2005, 74, 739-89), we addressed the role of AHLs in activation of the UPR by investigating if the spliced form of XBP1 mRNA (sXBP1) is generated in response to the presence of N-(3-oxo-acyl-dodecanoyl) homoserine lactone ("C12"). An RT-PCR assay revealed that compound C12 as well as other AHLs induced the generation of sXBP1 in mouse embryonic fibroblasts (MEFs) and the response to C12 was comparable with the effects of tunicamycin (Tg) and thapsagargin (Tg). This response to C12 was not limited to MEFs, but was also observed in a wide variety of cell types, including human transformed cells.

The bacterial super community, also referred to as the microbiota, coexists with multi-cellular organisms and is the ancient environment factor with important roles in numerous stress-sensing physiological processes, particularly those involved in metabolic and immune responses of the host cells. For example, the gut microbiota beneficially contributes to both the metabolic system by promoting the harvest of dietary nutrients[1, 2] and the immune system by maintaining the normal low-grade level of inflammation[2-4]. Traditionally, inflammatory process is required for tissue repair and involves integration of many complex signaling mechanisms including modulation of the Toll-like receptor (TLR) pathways in response to bacterial products such as lipopolysaccharide (LPS) and peptidoglycan[4, 5]. On the other hand, the microbiota-mediated inflammation is also associated with metabolic disorders such as obesity and cancer development[2, 6-8]. Although the molecular mechanisms underlining these disorders are inextricable interconnected with activation of the endoplasmic reticulum (ER) stress pathway[5, 9, 10], the bacterial component(s) triggering ER stress has yet to be identified.

Figure 1A:
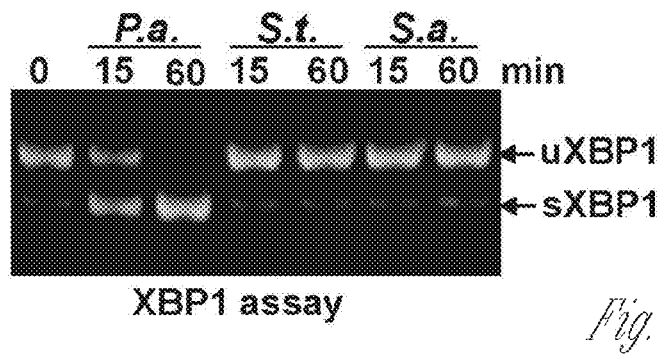
FIG. 1: C12 Induces the UPR in mammalian cells. (A and B). Comparison of the macrophage responsiveness to *P.* *aeruginosa* (P.a.), *S. typhimurium* (S.t.), and *S. aureus* (S.a.). RT-PCR assay of XBP1 (A) and Western blot analysis (B) of p38, its phosphorylated form (p-p38) as well as phosphorylated forms of PERK (p-PERK) and eIF2α(p-eIF2α) in cell extracts after treatment with bacteria are shown. (C) Macrophages were stimulated with *P. aeruginosa* wild type (wt) or lasI mutant (ΔlasI), and cell extracts (total RNA or total protein) were prepared and analyzed as in (A and B). (D and E) RT-PCR assay of XBP1 or actin in total RNA prepared from macrophages after treatment with compound (C12), i.e., the (S)-enantiomer, or with the (R)-enantiomer (C12R), or the hydrolysis product (C12h) are shown. (F) Total RNA was prepared from lung of mice after inoculation of vehicle (−) or (C12) and analyzed as in (D). (G) Chemical structures of compounds (C12), (C12R) and (C12h). Compound (C12) is the (S)-enantiomer of the compound of formula.
Figure 1B:
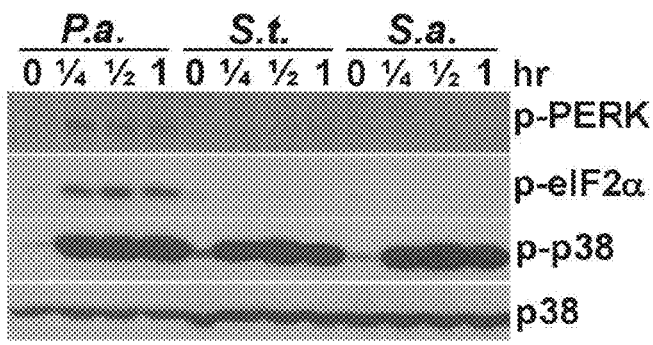
Figure 1C:
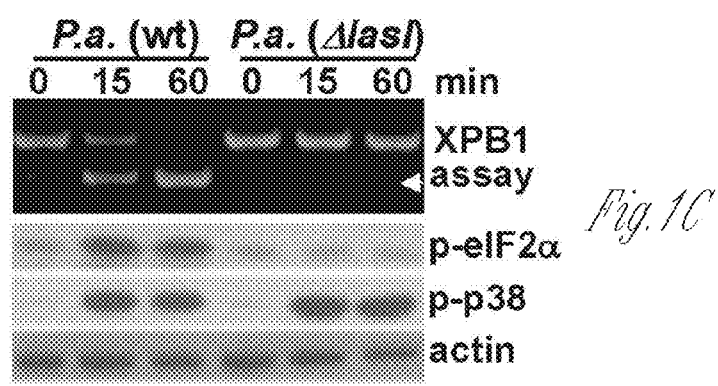
Figure 1D:
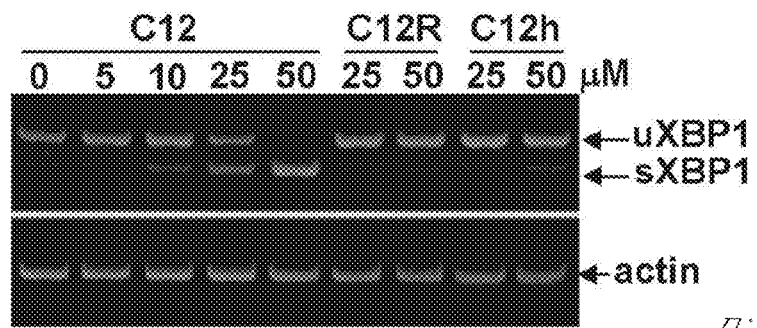

Among key biochemical signatures of the multicomponent ER stress pathway, known as the unfolded protein response (UPR), are the phosphorylation of the α-subunit of eukaryotic translation initiation factor-2 (eIF2α) and activation of the transcription factor XBP1/Hac1 (X-box binding protein-1 in metazoans and homologous to ATF/CREB in yeast, respectively)[11]. The ability of certain Gram-negative bacterium-derived molecules, such as N-(3-oxo-acyl) homoserine lactones (3-oxo-AHLs), to induce eIF2α phosphorylation[12] as well as the presence of 3-oxo-AHLs in samples of the microbiota[13-15] prompted us to investigate their role in activation of the UPR. The Gram-negative *Pseudomonas aeruginosa* and Gram-positive *Staphylooccus aureus* bacteria were chosen as two evolutionary distant microbes that can form part of human microbiota, and activate mammalian cells mainly through TLR4 and TLR2, respectively[4, 16]; unlike to *S. aureus, P. aeruginosa* also represents a class of bacteria synthesizing a prototypic member of the 3-oxo-AHL family, N-(3-oxo-dodecanoyl) homoserine lactone compound (C12). Additionally, the Gram-negative bacterium *Salmonella typhimurium* was used as a control microbe that contains TLR4 ligands similar to those in *P. aeruginosa*, but does not synthesize compound (C12)[17]. To initiate our studies, we exposed bone marrow-derived macrophages (BMDM) to these bacteria, and macrophage responsiveness was analyzed for biochemical markers of the UPR and the phosphorylation of the mitogen-activated protein kinase p38, as a common marker of TLR pathways. Rapid and robust generation of the spliced form of XBP1 mRNA (sXBP1) was observed in response to *P. aeruginosa*, whereas two other bacteria induced very faint, if any, level of sXBP1 (FIG. 1A). Moreover, although all three bacteria induced similar levels of p38 phosphorylation (p-p38), additional signs of the UPR, such as the phosphorylated forms of eIF2α and PERK [the double-stranded RNA-dependent protein kinase (PRK)-like ER kinase], were only observed in response to *P. aeruginosa* (FIG. 1B). Notably, we found that *P. aeruginosa* deficient in lasI, the gene responsible for compound (C12) synthesis, lost the ability to activate sXBP1 and eIF2α phosphorylation (FIG. 1C), providing evidence that the observed induction of the UPR markers was linked to the presence of C12 in wild type *P. aeruginosa*. Indeed, direct addition of C12 resulted in time- and dose-dependent induction of sXBP1 (FIGS. 1D and 1E). Such activation of the UPR was selective to the natural (S)-form of compound (C12), whereas an unnatural (R)-stereoisomer (C12R) or a hydrolyzed form of compound (C12), (C12h), was ineffective (FIGS. 1D and 1G).

Importantly, the similar requirements in the structural integrity of the lactone ring motif were also evident in response to other natural stereoisomer of the AHL family (Table 1). These effects of AHLs on the UPR activation were not limited to macrophages, but were also observed in other cell types including mouse embryonic fibroblasts (MEF), normal human bronchial epithelial cells and human TPH1 cell line (Table 2). More importantly, administration of C12 into mouse lung resulted in the generation of sXBP1 (FIG. 1F), consistent with our experiments in cultured cells. Thus, AHLs represent the first example of secreted bacterial molecules that possess the ability to induce the UPR in various mammalian cells.

Modulation of the Sphingolilid Metabolism by C12 Results in Activation of the UPR.

The unfolded protein response relies on both protein and lipid components of the ER[11]. To clarify whether C12 targets protein component of the ER, we examined the effect of a general protein synthesis inhibitor CHX on sXBP1 induction in response to C12, tunicamycin (Tm, an inhibitor of protein glycosylation affecting the folding of newly synthesized protein) or thapsigargin (Tg, an inducer of passive release of calcium from ER stores resulting to activation of the UPR independently from de novo protein synthesis). Compared to Tg and especially to Tm, C12-induced generation of sXBP1 was completely resistant to CHX (FIG. 2A), suggesting that a protein component of the ER stress is dispensable for the C12-induced UPR activation.

Figure 2A:
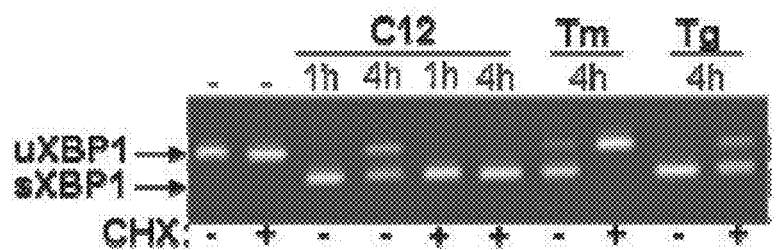
Figure 2B:
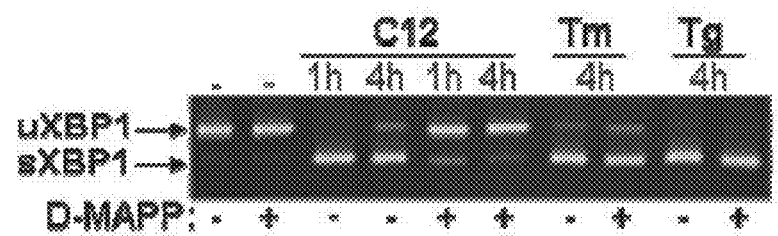
Figure 2C:
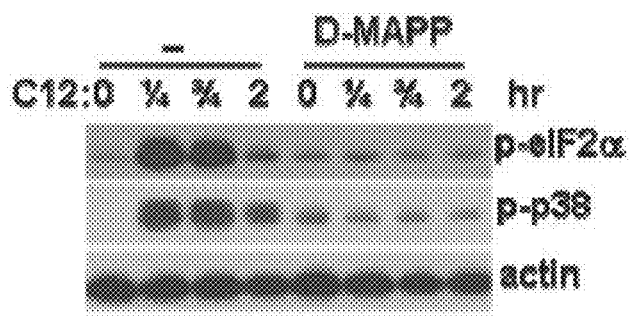
Figure 2D:
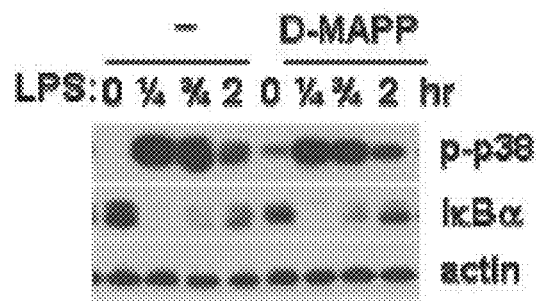

It has been suggested that the biosynthesis of lipids and regulation of the UPR are linked, although the specific lipid components involved in modulation of the UPR have not defined yet[10, 11, 18]. Since de novo synthesis of the core sphingolipid, N-acyl-spingosine or ceramide (Cer), occurs in the ER[10], we sought to test whether pharmacological inhibitors of sphingolipid metabolism alter the UPR activation by C12. The results of these experiments identified D-MAPP, an inhibitor of Cer cleavage, as an agent that substantially impaired C12-induced phosphorylation of eIF2α(FIG. 2B). The inhibitory effect was specific to C12-mediated UPR activation, as both Tm- and Tg-mediated induction of sXBP1 was unchanged in the presence of D-MAPP (FIG. 2C); additionally, LPS-induced activation of p38 phosphoylation and the profiles of IκBα expression were also unaltered by D-MAPP (FIG. 2D). Thus, these findings suggest that both IRE1 and PERK arms of the UPR sense and respond to changes in sphingolipid metabolism induced by C12.

Figure 2E:
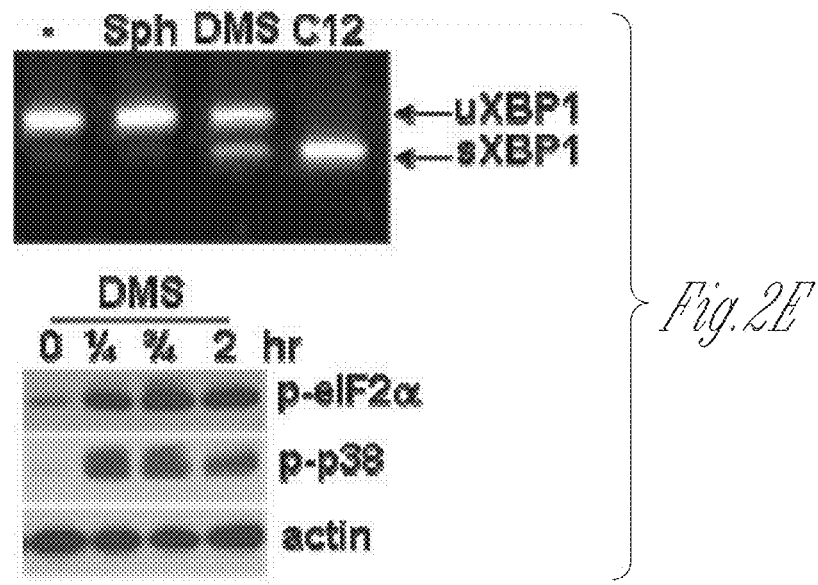
Figure 2F:
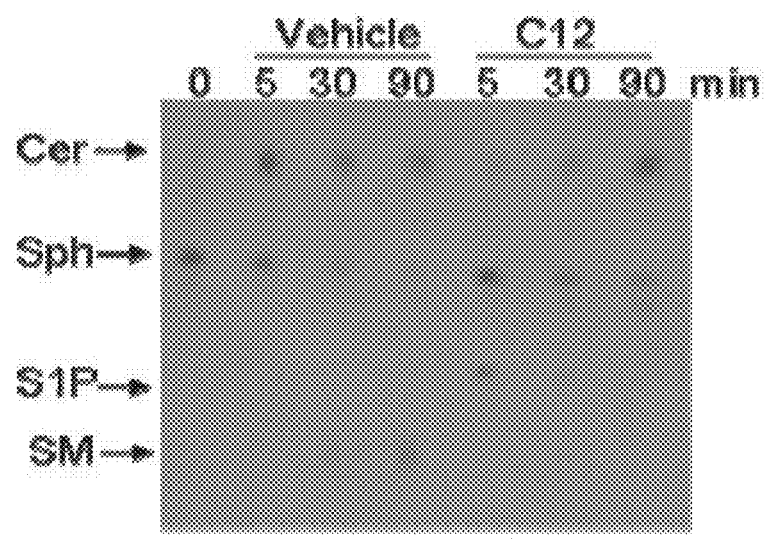

The backbone component of all sphingolipids, sphingosine (Sph), is a product of Cer cleavage. Acylation of the Sph amino group with fatty acids recycles Cer, whereas the phosphorylation of Sph results in production of spingosine 1-phosphate (S1P), hydrolysis of which represents the final step of the metabolic pathway[10, 19]. Sph also can be N-methylated to N,N-dimethylsphingosine (DMS) that acts as a naturally occurred inhibitor of the sphingosine kinase activity; and its addition to the cells results in a decrease in S1P and accompanies with small increase in Sph levels[20, 21]. Toward this end, our data showed that modulation of the Sph metabolism was correlated with the UPR activation, because the expected increase in intracellular Sph level due to DMS treatment resulted in the induction of sXBP1 and eIF2α phosphorylation, whereas the extracellular addition of Sph had no effect on these biochemical markers of the UPR (FIG. 2E). Therefore, to address whether C12 modulates metabolic conversion of intracellular Sph. BMDM were radiolabeled with $^3$H-Sph in the absence or presence of C12, and the distribution of radioactivity within the sphingolipid fractions was estimated by thin layer chromatography (TLC). We found that substantial amount of $^3$H-radioactivity was rapidly (within 5 min) incorporated into the Cer fraction, and two hours later, it was distributed between the ceramide and sphingomyelin (SM) fractions. Addition of C12 dramatically changed the early, as well as the late steps of sphingolipid metabolism; after 2 hr the expected incorporation into the sphingomyelin was not observed but rather the radioactivity remained in the sphingosine fraction (FIG. 2F). Moreover, a 5-min treatment with C12 also resulted in the incorporation of $^3$H-radioactivity into another fraction (presumably S1P) that diminished over time. Although further detailed studies of mechanisms involved in these processes are needed, these finding provide a first piece of evidence that C12 possesses the ability to modulate the metabolism of sphingolipids, perhaps through the steps involved in Sph turnover and generation, and this effect of C12 correlates with activation of the UPR. Thus, we postulate that C12 induces cell activation through modulation of the metabolism of sphingolipids.

C12 Possesses the Ability to Act as a Cancer-Stop and Cancer Preventing Agent.

Ceramide (Cer), sphingosine (Sph) and Sph-1-phospate (S1P) represent general signaling lipids with critical roles in defense mechanisms regulating apoptotic removal of damaged cells to prevent autoimmunity and cancer development[9, 10, 19, 22].

In eukaryotes, sphingolipids are synthesized de novo in the endoplasmic reticulum (ER) via biosynthetic pathway, in which N-acyl-spingosine or Cer is a core metabolite that can be further modified to produce sphingomyelins or more complex glycosphingolipids. In contrast to Cer, D-erytro-sphingosine (Sph) is formed only in a result of Cer cleavage, whereas acylation of the Sph amine group with fatty acids recycles the Cer. Moreover, although both phosphorylated products of Cer and Sph, C1P and S1P respectively, may be salvaged by dephosphorylation, S1P can be irreversibly cleaved. Once generated, these molecules become "bioactive" lipids that regulate the diverse cellular functions in a manner distinct from the canonical paradigm of the linear signaling pathway[10]. The unique complexity of sphingolipid signaling is not only in their metabolic interconvertion, but also is the opposite effect of individual bioactive lipids on given pathway. For example, Sph acts as a negative regulator of cell growth and promotes the stimuli-induced apoptotic pathways[21-24], while its phosphorylated counterpart SIP induces the cell proliferation and protects from apoptosis[22, 24, 25]. In fact, a number of environmental and endogenous factors/conditions alter the metabolism of sphingolipids[10]. Since several of these conditions are also associated with development and progression of metabolic diseases and cancer, it is logical to consider that an enhance of sphingolipid-mediated apoptotic signaling could stop the disease progressing from any stage if a given agent leaves healthy cells intact while inducing cancerous cells to self-destruct.

In this regard, the ability of C12 to affect Sph metabolism (see above FIG. 2) suggested that C12 acts as a potential cancer-stop and cancer preventing agent through selective activation of apoptosis in transformed cells or inflammation-damaged cells, such as macrophages that produces tumor necrosis factor (TNF), an inflammatory cytokine. Consistent with this assumption, our previously published data revealed that C12 treatment of myeloid cells results in rapid induction of apoptosis, although non-myeloid cells show significantly delayed kinetics and reduction of the apoptotic marker expression (see FIG. 3 in Kravchenko et al., 2006; ref #12).

Figure 3A:
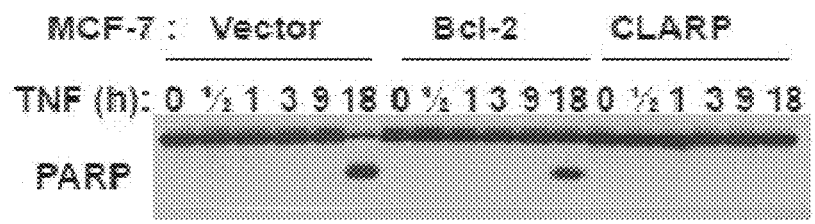
Figure 3B:
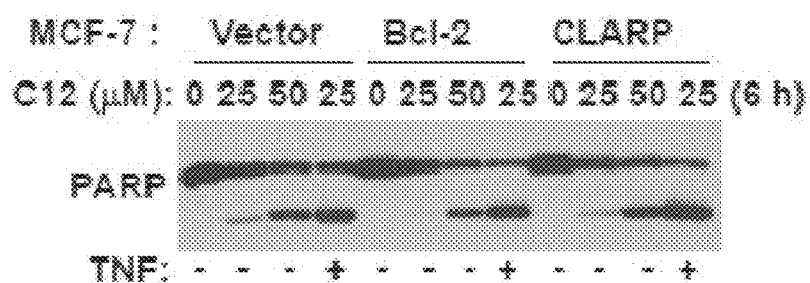

To further test this hypothesis, we compared sensitivity of breast cancer cell line MCF7 to apoptosis induced by TNF, C12 or their combination. In these experiments we used a control variant of MCF7 (Vector) as well as MCF7 cells stably expressing negative regulators of apoptosis, such as Bcl-2 and CLARP; Bcl-2 is an inhibitor of the intrinsic apoptotic pathway, whereas CLARP inhibits receptor-dependent apoptotic signaling, also called the extrinsic apoptotic pathway. The cells were incubated with TNF, C12 or their combination, and protein extracts were analyzed by Western blot for the cleavage of PARP, a biochemical marker indicative of apoptosis[26]. As expected, prolong incubation of control and MCF7/Bcl-2 cells with TNF induced the cleavage of PARP, whereas MCF7/CLARP cells were resistant to TNF-mediated apoptosis (FIG. 3A). In contrast, all three cell lines showed sensitivity to C12; also, the synergy between C12 and TNF was evident in all three cell lines treated by a combination of both stimuli (FIG. 3B).

Figure 3C:
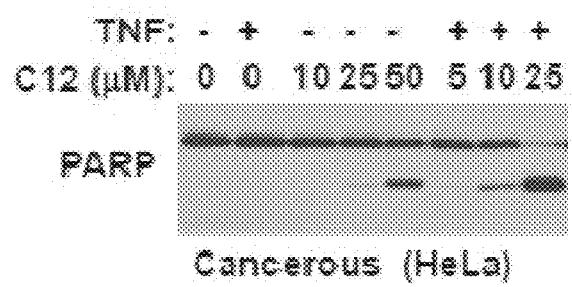
Figure 3D:
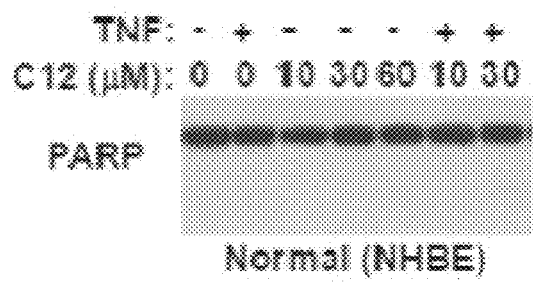

Similar experiments were conducted by using normal human bronchial epithelial cells and HeLa cell line as an example of transformed cells. We observed that both HeLa and normal cells were resistant to pro-apoptotic effects of TNF (FIGS. 3C and 3D). Normal cells also showed resistance to C12 and its combination with TNF (FIG. 3D), although C12 alone induced the cleavage of PARP in HeLa cells. Notably, strong synergism was observed between TNF and C12 in HeLa cells (see FIG. 3C). Thus, these data further support our assumption that C12 induces apoptosis in cancer cells, while normal cells are relatively resistant to C12 or its combination with TNF. In addition, two stimuli—C12 and TNF—work synergistically against cancerous cells, although normal cells stay intact.

A Combination of TRAIL and C12 or an Analog Synergistically Kills Cancerous Cells.

Among a promising candidate for cancer therapeutics is tumor necrosis factor (TNF)-related apoptosis-inducing ligand (TRAIL). Similar to other members of the TNF family, TRAIL initiates apoptosis through the receptor-mediated mechanism, also referred to as the extrinsic apoptotic pathway. In contrast to other naturally occurring pro-apoptotic ligands such as TNF and Fas ligand (FasL), TRAIL infusion into mice does not cause a lethal response or detectable toxicity to tissues and organs[27-29]. Furthermore, the potential significance of TRAIL for killing cancer cells has been supported by studies in animal models demonstrating that this cytokine possesses selective toxicity to human tumor xenografts but not normal tissues[28, 29]. However, sensitivity to TRAIL-induced apoptosis is a key factor limiting the efficacy of TRAIL treatment, because a spectrum of sensitivity is varied in different malignant cells[27, 28, 30]. Furthermore, similar to normal cells, some cancer cells are also resistant to TRAIL-induced apoptosis, although the basis for the sensitivity and resistance of cells to TRAIL-mediated effects is not fully understood.

The increasing understanding of the molecular details of apoptosis indicates that tumor cells can acquire resistance to apoptosis through interference with either extrinsic or intrinsic apoptotic signaling pathways, which commonly accompanies with defects in cell growth control or/and with an increase in the anti-apoptotic activity of survival pathways such as the NF-κB and Akt signaling cascades. Indeed, most cancer cells retain the capacity to carry out apoptosis if triggered through mechanisms that can overcome such anti-apoptotic activities. For example, inhibition of NF-κB activity significantly increases apoptosis induced by apoptotic stimuli[31-34]. In addition, enhancing apoptosis also occurs upon activation of several intracellular non-apoptotic signaling processes, including the JNK pathway or endoplasmic reticular (ER) stress, known in eukaryotic cells as the unfolded protein response (UPR)[11]. Remarkably, recent observations revealed that the UPR activators, such as tunicamycin (Tm), thapsigargin (Tg) and RRR-α-tocopherol ether-link acetic acid analog (α-TEA), sensitize cancer cells to TRAIL-induced apoptosis[35-37]. However, these reagents induce constitutive and sustained activation of the UPR, which usually results in the induction of the mitochondria-dependent intrinsic apoptotic pathways[38-40], even in the absence of pro-apoptotic stimuli such as TRAIL[37, 40].

Modern understanding of the intimate associations between host and the microbiota[41], suggest that microbes have evolved subtle and selective strategies to collaborate with host's biology[1, 42]. Normally many bacterial products induce inflammatory processes, which are a risk factor commonly associated with the development of cancer and autoimmune diseases[17, 43]. However, it is not a case for other bacterial molecules. For example, our recent findings revealed that C12 possesses strong anti-inflammatory activity[17]. Moreover, the realization that C12 also induces the UPR prompted us to explore its potential as a complement for anti-cancer therapy.

To test this hypothesis, we examined the effect of C12 in vitro on the activity of TRAIL against A549 cell line derived from a cancer sample of the human lung. Consistent with the reported observation on A549 cells[28](Ashkenazi A et al., 1999), in vitro addition of TRAIL (50 ng/ml) to the cultured A549 cells did not significantly affect their viability and growth. However, the viability of A549 cells were dramatically reduced when a combination of TRAIL (50 ng/ml) and C12 (1 µM) was added to the cultured medium (FIG. 4), although the cell growth and viability was practically unchanged in the presence of C12 (1 µM or 25 µM), its unnatural stereoisomer C12R (25 µM) or a combination of TRAIL (50 ng/ml) and C12R (25 M) (FIG. 4A). Titration experiments revealed that more then 50% of cells lost their viability after a 24-hours incubation in the cultured medium with 100 nM of C12 and 50 ng/ml of TRAIL (FIG. 4B). These data support our assumption that resistance to TRAIL-mediated apoptosis might be overcome in the presence of C12.

To address whether C12 increases the pro-apoptotic effect of TRAIL against cancerous cells, we compared responses of A549 cells to TRAIL, C12 or TRAIL+C12 by Western blot analysis for several biochemical parameters relevant to the regulation of apoptosis and cell growth as well as cellular stress responses. Namely, the cleavage of poly(ADP-ribose) polymerase (PARP) and caspase-3 were used as two common markers indicative of processes induced through both the extrinsic and intrinsic apoptotic pathways[26, 44]; we also examined the cleavage of caspase-9 as a marker indicative of the intrinsic apoptotic pathway[45]; activation of the protein kinase JNK pathway, a hallmark of the mammalian stress response linked to cell growth control[46-48], was tested by the analysis for the phosphorylation of JNK. To monitor the activity of C12, we analyzed the phosphorylation of eIF2α, a distinct feature of ER stress[11, 49], and the phosphorylation of the protein kinase p38, an additional marker of the mammalian stress response[50]. The results of these experiments revealed that the stimulation with C12 resulted in rapid and strong activation of the stress responses with similar kinetics for all three markers, although apoptotic signaling was not induced at any time point tested (FIG. 5). In contrast, TRAIL treatment was certainly calm for activation of eIF2α phosporylation and other markers of the stress responses, although we noted barely detectable p38 and JNK phosphorylation at 6-hour time point; also, we observed the expected activation of caspase-3 leading to subsequent cleavage of PARP (see FIG. 5). Notably, substantial changes of both the apoptotic and stress response markers were evident in cells treated with a combination of TRAIL and C12 at late time points (FIG. 5; compare the 2- and 6-hour time points).

Similar studies on a panel of other cancerous and normal cells confirmed these observations and demonstrated that C12 substantially sensitized different cancerous cells to TRAIL-mediated apoptosis, whereas normal cells were completely resistant (FIG. 6, FIG. 7 and Table 2), consistent with our previous observations when TNF was used instead of TRAIL (see above FIG. 3). Thus, reciprocal synergism between C12- and TRAIL- or TNF-mediated signaling results in prominent pro-apoptotic effect against cancerous cells, suggesting that the application of C12 might uncover new anti-cancer therapeutic strategies.

Bortezomid (also known as velcade) is an anti-cancer drug that strongly sensitizes cancerous cells to TRAIL-induced apoptosis[51-53]. Therefore, to assess a potential utility of C12 for anti-cancer therapy, we compared the effects of these two compounds—(C12) and bartezomid (Bor)—on TRAIL-mediated apoptosis in cancerous A549 cells and primary human hepatocytes. The comparable increase in sensitivity of A549 cells to TRAIL was observed in the presence of either Bor or (C12) (FIG. 8A, top penal); also, similar levels of PARP cleavage (an apoptotic marker) were induced in response to a combination of TRAIL with Bor or (C12) (FIG. 7, bottom panel). Viability of normal human hepatocytes was unchanged in the presence of TRAIL (FIG. 8B, top penal); also, TRAIL-treated hepatocytes exhibited no evidence of apoptosis (FIG. 8B bottom panel). Similar examination of Bor-treated samples revealed that although this drug alone exhibited relatively low levels of toxicity toward hepatocytes, Bor-mediated toxicity as well as Bor-induced apoptosis was substantially enhanced in the presence of TRAIL (see FIG. 8B). In contrast, the hepatocytes were practically healthy and intact in the presence of (C12) or its combination with TRAIL (see FIG. 8B). Thus, (C12) possesses potent anticancer activity without significant toxicity toward non-cancerous cells.

Since (C12) is a prototypic member of the 3-oxo-AHL family, the structure-activity-relation (SAR) investigations were warranted to determine generic structural features of AHL, which are required for a cancer-stop and cancer preventing activity as well as for activation of the UPR. To address this questions, a set of AHLs and their analogs were synthesized (see List of AHLs and analogs), and the biological activity of all compounds were examined on a panel of cancerous and normal cells. The prototypic examples of biochemical data for the selected analogs are shown in FIG. 9 and FIG. 10, whereas Table 2 summarizes the SAR studies for all compounds. These comprehensive SAR studies identified several analogs (13, 15 and 16, see Table 1, below) of (C12), which possess (C12)-like effect on mammalian cells. Moreover, similar to (C12), all three analogs strongly sensitize a number of cancerous cells to TRAIL-mediated apoptosis, suggesting that their application might lead to new anti-cancer therapeutic strategies.

DOCUMENTS CITED

1. Backhed, F.; Ley, R. E.; Sonnenburg, J. L.; Peterson, D. A.; Gordon, J. I., Host-bacterial mutualism in the human intestine. *Science* 2005, 307 (5717), 1915-20.
2. Cani, P. D.; Delzenne, N. M., Gut microflora as a target for energy and metabolic homeostasis. *Curr Opin Clin Nutr Metab Care* 2007, 10 (6), 729-34.
3. Cebra, J. J., Influences of microbiota on intestinal immune system development. *Am J Clin Nutr* 1999, 69 (5), 1046S-1051S.
4. Janeway, C. A., Jr.; Medzhitov. R., Innate immune recognition. *Annu Rev Immunol* 2002, 20, 197-216.
5. Hotamisligil, G. S., Inflammation and metabolic disorders. *Nature* 2006, 444 (7121), 860-7.
6. Maslowski, K. M.; Mackay, C. R., Diet, gut microbiota and immune responses. *Nat Immunol* 12 (1), 5-9.
7. Wolowczuk, I.; Verwaerde, C.; Viltart, O.; Delanoye, A.; Delacre, M.; Pot, B.; Grangette, C., Feeding our immune system: impact on metabolism. *Clin Dev Immunol* 2008, 2008, 639803.
8. Ley, R. E.; Turnbaugh, P. J.; Klein, S.; Gordon, J. I., Microbial ecology: human gut microbes associated with obesity. *Nature* 2006, 444 (7122), 1022-3.
9. Hotamisligil, G. S.; Erbay, E., Nutrient sensing and inflammation in metabolic diseases. *Nat Rev Immunol* 2008, 8 (12), 923-34.
10. Hannun, Y. A.; Obeid, L. M., Principles of bioactive lipid signalling: lessons from sphingolipids. *Nat Rev Mol Cell Biol* 2008, 9 (2), 139-50.
11. Ron, D.; Walter, P., Signal integration in the endoplasmic reticulum unfolded protein response. *Nat Rev Mol Cell Biol* 2007, 8 (7), 519-29.
12. Kravchenko, V. V.; Kaufmann, G. F.; Mathison, J. C.; Scott, D. A.; Katz, A. Z.; Wood, M. R.; Brogan, A. P.; Lehmann, M.; Mee, J. M.; Iwata, K.; Pan, Q.; Fearns, C.; Knaus, U. G.; Meijler, M. M.; Janda, K. D.; Ulevitch, R. J., N-(3-oxo-acyl)homoserine lactones signal cell activation through a mechanism distinct from the canonical pathogen-associated molecular pattern recognition receptor pathways. *J Biol Chem* 2006, 281 (39), 28822-30.
13. Edrington, T. S.; Farrow, R. L.; Sperandio, V.; Hughes, D. T.; Lawrence, T. E.; Callaway, T. R.; Anderson, R. C.; Nisbet. D. J., Acyl-homoserine-lactone autoinducer in the gastrointestinal [corrected] tract of feedlot cattle and correlation to season, E. coli O157:H7 prevalence, and diet. *Curr Microbiol* 2009, 58 (3), 227-32.
14. Kumari, A.; Pasini, P.; Daunert, S., Detection of bacterial quorum sensing N-acyl homoserine lactones in clinical samples. *Anal Bioanal Chem* 2008, 391 (5), 1619-27.
15. Hughes. D. T.; Terekhova, D. A.; Liou, L.; Hovde, C. J.; Sahl, J. W.; Patankar, A. V.; Gonzalez, J. E.; Edrington, T. S.; Rasko, D. A.; Sperandio, V., Chemical sensing in mammalian host-bacterial commensal associations. *Proc Natl Acad Sci USA* 107 (21), 9831-6.
16. Irazoqui, J. E.; Troemel, E. R.; Feinbaum, R. L.; Luhachack, L. G.; Cezairliyan, B. O.; Ausubel, F. M., Distinct pathogenesis and host responses during infection of C. elegans by P. aeruginosa and S. aureus. *PLoS Pathog* 6, e1000982.
17. Kravchenko, V. V.; Kaufmann, G. F.; Mathison, J. C.; Scott, D. A.; Katz, A. Z.; Grauer, D. C.; Lehmann, M.; Meijler, M. M.; Janda, K. D.; Ulevitch, R. J., Modulation of gene expression via disruption of NF-kappaB signaling by a bacterial small molecule. *Science* 2008, 321 (5886), 259-63.
18. Cox, J. S.; Chapman, R. E.; Walter, P., The unfolded protein response coordinates the production of endoplasmic reticulum protein and endoplasmic reticulum membrane. *Mol Biol Cell* 1997, 8 (9), 1805-14.
19. Merrill, A. H., Jr., De novo sphingolipid biosynthesis: a necessary, but dangerous, pathway. *J Biol Chem* 2002, 277 (29), 25843-6.
20. Yatomi, Y.; Ruan, F.; Megidish, T.; Toyokuni, T.; Hakomori, S.; Igarashi, Y., N,N-dimethylsphingosine inhibition of sphingosine kinase and sphingosine 1-phosphate activity in human platelets. *Biochemistry* 1996, 35 (2), 626-33.
21. Suzuki, E.; Handa, K.; Toledo, M. S.; Hakomori, S., Sphingosine-dependent apoptosis: a unified concept based on multiple mechanisms operating in concert. *Proc Natl Acad Sci USA* 2004, 101 (41), 14788-93.
22. Cuvillier, O., Sphingosine in apoptosis signaling. *Biochim Biophvs Acta* 2002, 1585 (2-3), 153-62.
23. Ohta, H.; Yatomi, Y.; Sweeney, E. A.; Hakomori, S.; Igarashi, Y., A possible role of sphingosine in induction of apoptosis by tumor necrosis factor-alpha in human neutrophils. *FEBS Lett* 1994, 355 (3), 267-70.
24. Spiegel, S.; Milstien, S., Sphingosine-1-phosphate: signaling inside and out. *FEBS Lett* 2000, 476 (1-2), 55-7.
25. Spiegel, S., Sphingosine 1-phosphate: a ligand for the EDG-1 family of G-protein-coupled receptors. *Ann N Y Acad Sci* 2000, 905, 54-60.
26. Nicholson, D. W.; All, A.; Thornberry, N. A.; Vaillancourt, J. P.; Ding, C. K.; Gallant, M.; Gareau, Y.; Griffin, P. R.; Labelle, M.; Lazebnik, Y. A.; et al., Identification and inhibition of the ICE/CED-3 protease necessary for mammalian apoptosis. *Nature* 1995, 376 (6535), 37-43.

27. Ashkenazi, A., Directing cancer cells to self-destruct with pro-apoptotic receptor agonists. *Nat Rev Drug Discov* 2008, 7 (12), 1001-12.
28. Ashkenazi, A.; Pai, R. C.; Fong, S.; Leung, S.; Lawrence, D. A.; Marsters, S. A.; Blackie, C.; Chang, L.; McMurtrey, A. E.; Hebert, A.; DeForge, L.; Koumenis, I. L.; Lewis, D.; Harris, L.; Bussiere, J.; Koeppen, H.; Shahrokh, Z.; Schwall, R. H., Safety and antitumor activity of recombinant soluble Apo2 ligand. *J Clin Invest* 1999, 104 (2), 155-62.
29. Walczak, H.; Miller, R. E.; Ariail, K.; Gliniak, B.; Griffith, T. S.; Kubin, M.; Chin, W.; Jones. J.; Woodward, A.; Le, T.; Smith, C.; Smolak, P.; Goodwin, R. G.; Rauch, C. T.; Schuh, J. C.; Lynch, D. H., Tumoricidal activity of tumor necrosis factor-related apoptosis-inducing ligand in vivo. *Nat Med* 1999, 5 (2), 157-63.
30. Lippa, M. S.; Strockbine, L. D.; Le, T. T.; Branstetter, D. G.; Strathdee, C. A.; Holland. P. M., Expression of anti-apoptotic factors modulates Apo2L/TRAIL resistance in colon carcinoma cells. *Apoptosis* 2007, 12 (8), 1465-78.
31. Beg, A. A.; Baltimore, D., An essential role for NF-kappaB in preventing TNF-alpha-induced cell death. *Science* 1996, 274 (5288), 782-4.
32. Wang, C. Y.; Mayo, M. W.; Baldwin, A. S., Jr., TNF- and cancer therapy-induced apoptosis: potentiation by inhibition of NF-kappaB. *Science* 1996, 274 (5288), 784-7.
33. Van Antwerp, D. J.; Martin, S. J.; Kafri, T.; Green, D. R.; Verma, I. M., Suppression of TNF-alpha-induced apoptosis by NF-kappaB. *Science* 1996, 274 (5288), 787-9.
34. Liu, Z. G.; Hsu, H.; Goeddel, D. V.; Karin, M., Dissection of TNF receptor 1 effector functions: JNK activation is not linked to apoptosis while NF-kappaB activation prevents cell death. *Cell* 1996, 87 (3), 565-76.
35. Jiang, C. C.; Chen, L. H.; Gillespie, S.; Kiejda, K. A.; Mhaidat, N.; Wang, Y. F.; Thorne, R.; Zhang, X. D.; Hersey, P., Tunicamycin sensitizes human melanoma cells to tumor necrosis factor-related apoptosis-inducing ligand-induced apoptosis by up-regulation of TRAIL-R2 via the unfolded protein response. *Cancer Res* 2007, 67 (12), 5880-8.
36. Chen, L. H.; Jiang, C. C.; Kiejda, K. A.; Wang, Y. F.; Thorne, R. F.; Zhang, X. D.; Hersey, P., Thapsigargin sensitizes human melanoma cells to TRAIL-induced apoptosis by up-regulation of TRAIL-R2 through the unfolded protein response. *Carcinogenesis* 2007, 28 (11), 2328-36.
37. Tiwary, R.; Yu, W.; Li, J.; Park, S. K.; Sanders, B. G.; Kline, K., Role of endoplasmic reticulum stress in alpha-TEA mediated TRAIL/DR5 death receptor dependent apoptosis. *PLoS One* 5 (7), e11865.
38. Szegezdi, E.; Logue, S. E.; Gorman, A. M.; Samali, A., Mediators of endoplasmic reticulum stress-induced apoptosis. *EMBO Rep* 2006, 7 (9), 880-5.
39. Gupta, S.; Cuffe, L.; Szegezdi, E.; Logue, S. E.; Neary, C.; Healy, S.; Samali, A., Mechanisms of ER Stress-Mediated Mitochondrial Membrane Permeabilization. *Int J Cell Biol* 2010, 170215.
40. Szegezdi, E.; Cahill, S.; Meyer, M.; O'Dwyer, M.; Samali, A., TRAIL sensitisation by arsenic trioxide is caspase-8 dependent and involves modulation of death receptor components and Akt. *Br J Cancer* 2006, 94 (3), 398-406.
41. Savage, D. C., Microbial ecology of the gastrointestinal tract. *Annu Rev Microbiol* 1977, 31, 107-33.
42. Hsiao, W. W.; Metz, C.; Singh. D. P.; Roth, J., The microbes of the intestine: an introduction to their metabolic and signaling capabilities. *Endocrinol Metab Clin North Am* 2008, 37 (4), 857-71.
43. Telford, G.; Wheeler, D.; Williams, P.; Tomkins, P. T.; Appleby, P.; Sewell, H.; Stewart, G. S.; Bycroft, B. W.; Pritchard, D. I., The *Pseudomonas aeruginosa* quorum-sensing signal molecule N-(3-oxododecanoyl)-L-homoserine lactone has immunomodulatory activity. *Inject Immun* 1998, 66 (1), 36-42.
44. Gyrd-Hansen, M.; Meier, P., IAPs: from caspase inhibitors to modulators of NF-kappaB, inflammation and cancer. *Nat Rev Cancer* 10 (8), 561-74.
45. Green, D. R.; Reed, J. C., Mitochondria and apoptosis. *Science* 1998, 281 (5381), 1309-12.
46. Brenner, D. A.; O'Hara, M.; Angel, P.; Chojkier, M.; Karin, M., Prolonged activation of jun and collagenase genes by tumour necrosis factor-alpha. *Nature* 1989, 337 (6208), 661-3.
47. Schreiber, M.; Kolbus, A.; Piu, F.; Szabowski, A.; Mohle-Steinlein. U.; Tian, J.; Karin, M.; Angel, P.; Wagner, E. F., Control of cell cycle progression by c-Jun is p53 dependent. *Genes Dev* 1999, 13 (5), 607-19.
48. Shaulian, E.; Schreiber, M.; Piu, F.; Beeche, M.; Wagner, E. F.; Karin, M., The mammalian UV response: c-Jun induction is required for exit from p53-imposed growth arrest. *Cell* 2000, 103 (6). 897-907.
49. Schroder, M.; Kaufman, R. J., The mammalian unfolded protein response. *Annu Rev Biochem* 2005, 74, 739-89.
50. Ono, K.; Han, J., The p38 signal transduction pathway: activation and function. *Cell Signal* 2000, 12 (1), 1-13.
51. Christian, P. A.; Thorpe, J. A.; Schwarze, S. R., Velcade sensitizes prostate cancer cells to TRAIL induced apoptosis and suppresses tumor growth in vivo. *Cancer Biol Ther* 2009, 8 (1), 73-80.
52. Arpinati, M.; Chirumbolo, G.; Nicolini, B.; Agostinelli, C.; Rondelli, D., Selective apoptosis of monocytes and monocyte-derived DCs induced by bortezomib (Velcade). *Bone Marrow Transplant* 2009, 43 (3), 253-9.
53. Pandit, B.; Gartel, A. L., Proteasome inhibitors induce p53-independent apoptosis in human cancer cells. *Am J Pathol* 178 (1), 355-60.

TABLE 1

Compounds Evaluated

| Compound # | Structure | LogP (est.) |
|---|---|---|
| 1 C12 | 3-oxo-C12-homoserine lactone (S) | 2.685 |
| 2 C12R | 3-oxo-C12-homoserine lactone (R) | 2.685 |
| 3 | 3-oxo-C8-homoserine lactone (S) | 0.569 |
| 4 | 3-oxo-C10-homoserine lactone (S) | 1.627 |
| 5 | 3-oxo-C14-homoserine lactone (S) | 3.743 |
| 6 | 3-oxo-C14-homoserine lactone (R) | 3.743 |
| 7 | 3-oxo-C12-homoserine lactam (S) | 2.569 |
| 8 | C12-homoserine lactone (S) | 3.718 |
| 9 | C4-homoserine lactone (S) | −0.514 |
| 10 | 3-oxo-C12-homoserine β-lactone (S) | 3.299 |

TABLE 1-continued

Compounds Evaluated

| Compound # | Structure | LogP (est.) |
|---|---|---|
| 11 | HC≡C-(CH2)7-C(O)-CH2-C(O)-NH-[(S)-homoserine lactone] | 1.856 |
| 12 | HC≡C-(CH2)4-C(O)-CH2-C(O)-NH-[(S)-homoserine lactone] | −0.26 |
| 13 (12-N3-12) | N3-(CH2)11-C(O)-CH2-C(O)-NH-[(S)-homoserine lactone] | 2.958 |
| 14 | N3-(CH2)11-C(O)-CH2-C(O)-NH-[(R)-homoserine lactone] | 2.958 |
| 15 3-N2 | CH3-(CH2)8-C(N2)-CH2-C(O)-NH-[(S)-homoserine lactone] (diazirine) | 3.202 |
| 16 12-N3-3-N2 | N3-(CH2)10-C(N2)-CH2-C(O)-NH-[(S)-homoserine lactone] (diazirine) | 3.475 |
| 17 12-N3-6-N2-12 | N3-(CH2)5-C(N2)-(CH2)2-C(O)-CH2-C(O)-NH-[(S)-homoserine lactone] (diazirine) | 1.71 |
| 18 | HC≡C-(CH2)6-C(N2)-(CH2)2-C(O)-CH2-C(O)-NH-[(S)-homoserine lactone] (diazirine) | 0.079 |
| 19 | CH3-(CH2)7-C(OH)(H)-CH2-C(O)-NH-[(S)-homoserine lactone] (3R-OH) | 2.64 |

TABLE 1-continued

Compounds Evaluated

| Compound # | Structure | LogP (est.) |
|---|---|---|
| 20 | [structure: long alkyl chain with OH, C(=O)NH-homoserine lactone] | 2.64 |

TABLE 2

Biological activities of compounds (naturally occurring or synthetic derivatives of N-acylhomoserine lactones) synthesized for structure-activity-relation studies in mammalian cells.

| Compound | Natural (n) or synthetic (s) | Efficiency of PARP cleavage (%)* | Efficiency of the p38 activation (%)* | Efficiency of the UPR activation (%)* | Effect on cancer cells: synergy with TRAIL or TNF |
|---|---|---|---|---|---|
| 1 | n | 100 | 100 | 100 | ++++ |
| 2 | s | <0.1 | <0.1 | <0.1 | − |
| 3 | n | <0.1 | <0.1 | <0.1 | n.d. |
| 4 | n | ~0.5 | ~2.0 | ~5.0 | + |
| 5 | n | >100 | >100 | >100 | ++++ |
| 6 | s | <0.1 | <0.1 | <0.1 | − |
| 7 | s | <0.1 | <0.1 | <0.1 | − |
| 8 | n | <0.1 | <0.1 | <0.1 | − |
| 9 | n | <0.1 | <0.1 | <0.1 | − |
| 10 | s | ~10.0 | ~2.0 | ~1.0 | n.d. |
| 11 | s | ~1.0 | ~2.0 | ~2.0 | n.d. |
| 12 | s | <0.1 | <0.1 | <0.1 | − |
| 13 | s | ~100 | ~100 | ~100 | ++++ |
| 14 | s | <0.1 | <0.1 | <0.1 | − |
| 15 | s | ~30.0 | ~40.0 | ~40.0 | +++ |
| 16 | s | ~60.0 | ~50.0 | ~70.0 | ++++ |
| 17 | s | ~10.0 | ~5.0 | ~10.0 | + |
| 18 | s | ~5.0 | ~2.0 | ~2.0 | n.d. |
| 19 | s | <0.1 | <0.1 | <0.1 | − |
| 20 | n | ~1.0 | ~2.0 | ~2.0 | + |

*The activity of a compound was normalized to those for N-(3-oxo-dodecanoyl) homoserine lactone (compound # 1, also abbreviated in the text as (C12)).

MATERIALS AND METHODS

A. General Methods

Cancer and Normal Cell Culture.

Lung cancer cell line A549 and colon cancer cell line HT29 were purchased from ATCC. Breast cancer cell line MDA-MB-468 was received from J. C. Reed (The Burnham Institute, La Jolla, Calif.). Cell lines were maintained in growth medium (GM): DMEM medium (4.5 g/l glucose) supplemented with 10% FBS (HyClone, Logan, Utah), L-glutamine, penicillin/streptomycin and nonessential amino acids (Invitrogen, Carlsbad, Calif.). Normal human bronchial epithelial (NHBE) cells and normal human mammary epithelial (NHME) cells were obtained from Cambrex (East Rutherford, N.J.) and cultured as recommended by the manufacturer. Normal human colon smooth muscle cells were obtained from ScienCell Research Lab (San Diego, Calif.) and cultured as recommended by the manufacturer. Primary cultures of human hepatocytes (freshly plated; not cryopreserved) and culture medium were obtained from Celsis In Vitro Technologies (Baltimore, Md.). Upon receipt of the cells, the medium was gently aspirated from each well and replenished with InVitroGRO HI medium supplemented with Torpedo Antibiotic Mix (Celsis), and the plates were kept in a 5% $CO_2$, at 37° C. in an incubator at saturating humidity. After 2-4 h, cells were stimulated as described in the text and figure legends.

Mice, Bone Marrow-Derived Macrophages and Other Cell Culture.

C57BL/6 mice were purchased from the Jackson Laboratory (Bar Harbor, Me.). Bone marrow-derived macrophages (BMDM) and murine embryonic fibroblasts (MEF) were prepared by using standard protocols that were approved by the TSRI Animal Care and Use Committee. L929/NCTC clone 929 (connective tissue, mouse) cell lines were purchased from ATCC (Manassas, Va.). MEFs and L929 cell line were maintained in GM (see above). BMDM were cultured in 70% GM and 30% L929 conditioned medium. In general, cells (~60-70% confluence) were incubated in fresh medium for 12-14 h before stimulation.

Bacterial Culture.

*Pseudomonas aeruginosa* bacterial strains used in our studies were kindly provided by Dr. Scott A. Beatson, University of Queensland, Brisbane, Australia and include wild type *Pseudomonas aeruginosa* PAO1 (originally from ATCC) and PAO1 ΔlasI. Bacterial strains used for control studies include *Acinetobacter baumannii*, *Escherichia coli*, *Staphylococcus aureus* and *Salmonella ryphimurium*, all from ATCC.

Reagents and Standard Assay.

Recombinant human TRAIL was purchased from R&D System, Inc (Minneapolis, Minn.), and was used for cell stimulation in all experiments at a concentration of 20 ng/ml or as indicated in the figure legends. Bacterial culture of *E. coli* expressing recombinant protein, a variant 118-291 of mTRAIL, was used for the preparation of recombinant murine TRAIL isolated by standard ion-exchange chromatography on DE52 and hydroxyapatite. *S. minnesota* Re595 LPS was prepared as previously described.[E1] All acylhomoserine lactones, including N-(3-oxododecanoyl)-S- and -R-homoserine lactone (C12 and C12R, respectively), were synthesized and purified as previously described.[E2] The purity was greater than 99% and was confirmed by HPLC/mass spectrometry analysis. All synthetic molecules were dissolved in DMSO at 200× of the desired concentration and aliquots were stored at −20° C. In addition, a quantitative QCL-1,000 chromogenic Limulus amoebocyte lysate assay (BioWhittaker, Walkersville, Md.) demonstrated that preparations of C12 were endotoxin free. Supernatant levels of TNF in the samples were measured by ELISA (BD Biosciences Pharmingen, San Diego, Calif.). Total RNA was isolated by using TRizol reagent (Invitrogen).

Antibodies and Western Blot Analysis.

Anti-eIF2α, phospho-eIF2α(p-eIF2α), p38, p-p38 (Thr180/Tyr132), p-RelA (Ser536), p-I κBSer32/36), PARP antibodies were purchased from Cell Signaling; anti-RelA, I κB α, IκBβ were from Santa Cruz Biotechnology. Cellular extracts were prepared and analyzed by Western blot assay as previously described.[E3]

Data Presentation.

The data depicted in FIGS. 11-13 represent one of three or more experiments with each graph reflecting findings typical of multiple studies.

General Chemistry Methods:

Reactions were carried out under a nitrogen atmosphere with dry, freshly distilled solvents under anhydrous conditions, unless otherwise noted. Methylene chloride ($CH_2Cl_2$) was distilled from calcium hydride. Tetrahydrofuran (THF) was distilled from sodium-benzophenone. Yields refer to chromatographically and spectroscopically homogenous materials, unless otherwise stated. Reactions were monitored by thin-layer chromatography (TLC) carried out on 0.25-mm EMD silica gel plates (60F-254) using anisaldehyde, $KMnO_4$ or PMA staining. Flash chromatography separations were performed on Silicycle silica gel (40-63 mesh). NMR spectra were recorded on Bruker 400 MHz spectrometers and calibrated using a solvent peak as an internal reference. The following abbreviations are used to indicate the multiplicities: s, singlet; d, doublet; t, triplet; q, quartet; m, multiplet; br, broad.

Chemistry Materials:

(S)-α-Amino-γ-butyrolactone was purchased from Aldrich and used as received.

B. Synthetic Procedures and Characterization Data
($3-N_2$)
Synthesis of the 3-diazirine derivative of C12

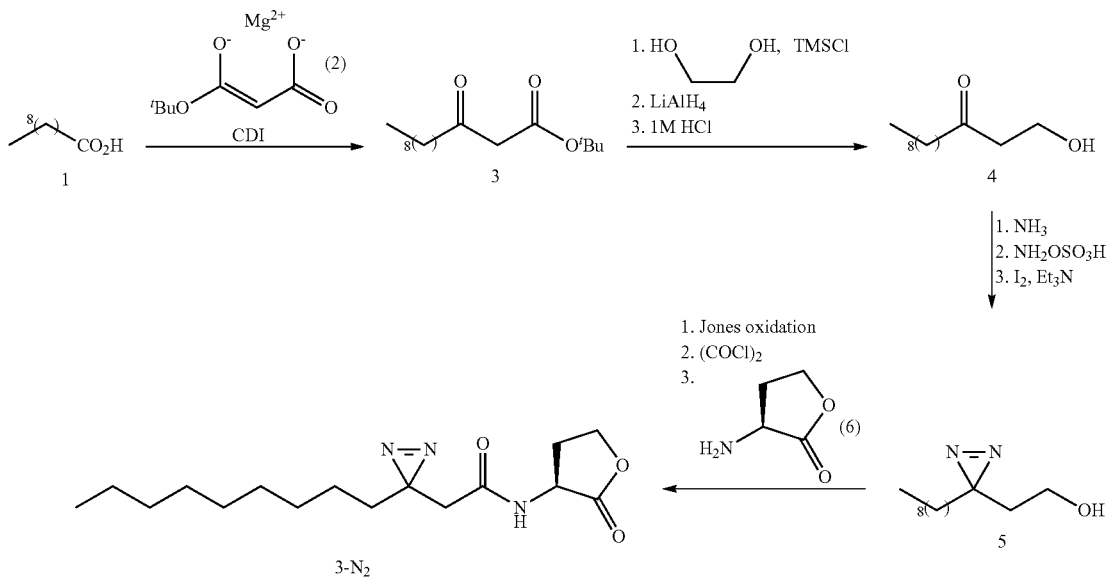

Preparation of 3.

Decanoic acid 1 (700 mg, 4.06 mmol) was added to a round-bottom flask and dissolved in THF (5.0 mL) under nitrogen atmosphere at 25° C. CDI (725 mg, 4.47 mmol) was then added and the resulting mixture was stirred at 25° C. for 4 h. In a second round-bottom flask, t-butyl malonate (716 mg, 4.47 mmol) was dissolved in THF (4.0 mL) under nitrogen atmosphere at 25° C. The flask was cooled to 0° C. and isopropyl magnesium chloride (4.5 mL, 2.0 M in THF, 8.93 mmol) was then added dropwise. The resulting mixture was stirred at 0° C. for 30 min and then warmed to 50° C. for 30 min. After cooling to 0° C., the decanoic acid solution was added via cannula and stirred from 0° C.-25° C. overnight. The reaction was then quenched with 1 M HCl (10 mL) and extracted with EtOAc (2×20 mL). The combined organic phases were washed with brine, dried with $Na_2SO_4$ and concentrated in vacuo. The resulting residue was purified by flash column chromatography (98:2 hexanes in EtOAc) to obtain 3 (950 mg, 86% yield). The characterization data for 3 matched that previously reported.[E4] $^1$H NMR (400 MHz, CDCl$_3$, 25° C.): δ=3.31 (s, 2H), 2.48 (t, 2H, J=7.2 Hz), 1.56-1.53 (m, 2H), 1.44 (s, 9H), 1.21-1.18 (m, 12H), 0.85 (t, 3H, J=6.8 Hz).

Preparation of 4.

Compound 3 (1.34 g, 5.0 mmol) was added to a round-bottom flask at 25° C. and dissolved in ethylene glycol (910 mg, 14.75 mmol) and methylene chloride (30 mL). TMSCl (3.2 g, 3.7 mL, 29.5 mmol) was then added to the stirring solution dropwise at 25° C. The resulting mixture was stirred for 4 days at 25° C. and then quenched with water (15 mL) and extracted with methylene chloride (2×20 mL). The combined organic phases were dried with Na$_2$SO$_4$ and concentrated in vacuo. This protected material was used as crude for the subsequent reaction. Crude ethylene glycol-protected 3 was added to a round-bottom flask and dissolved in THF (40 mL) under nitrogen atmosphere at 0° C. Lithium aluminum hydride (1.0 M in hexane, 1.5 equiv) was added dropwise, and the reaction mixture was allowed to warm to 25° C. After stirring for 4 h, the reaction was quenched with water and filtered. The filtrate was concentrated to ~20 mL, 1 M HCl (20 mL) was added and the mixture was stirred overnight at 25° C. The reaction mixture was then extracted with EtOAc (2×30 mL), and the combined organic phases were dried with Na$_2$SO$_4$ and concentrated in vacuo. The resulting residue was purified by flash column chromatography (3:1 hexanes in EtOAc) to obtain 4 (1.0 g, 80% yield over 3 steps). The characterization data for 4 matched that previously reported.[E5] $^1$H NMR (400 MHz, CDCl$_3$, 25° C.): δ=3.82 (t, 2H, J=5.4 Hz), 2.64 (t, 2H, J=5.2 Hz), 2.39 (t, 2H, J=5.2 Hz), 1.56-1.54 (m, 2H), 1.26-1.23 (m, 12H), 0.86 (t, 3H, J=6.8 Hz).

Preparation of 5.

The protocol for diazirine installation followed that previously reported.[3] Compound 4 (489 mg, 2.44 mmol) was added to a round bottom flash equipped with a condenser and dissolved in methanol (8 mL). Liquid ammonia (30 mL) was added, and the stirring solution was heated to reflux for 7 h. The resulting mixture was cooled in a dry ice-acetone bath, and a solution of NH$_2$OSO$_3$H (332 mg, 2.93 mmol) in methanol (10 mL) was added over 5 min. The cooling bath was removed, and the mixture was heated to reflux for 1 h. Following overnight evaporation of the liquid ammonia, the reaction mixture was filtered, and the filter cake was washed with methanol. The filtrate and washings were concentrated in vacuo, and the crude diazirine was used as crude for the subsequent oxidation reaction. Oxidation of the crude diaziridine to diazirine 5 was performed using the iodine-Et$_3$N method previously described,[E6] and the compound was obtained following flash column chromatography (120 mg, 23% yield). $^1$H NMR (400 MHz, CDCl$_3$, 25° C.): δ=3.44 (t, 2H, J=6.4 Hz), 1.64 (t, 2H, J=6.4 Hz), 1.37 (t, 2H, J=6.4 Hz), 1.26-1.17 (m, 14H), 0.87 (t, 3H, J=6.8 Hz); $^{13}$C NMR (100 MHz, CDCl$_3$, 25° C.): δ=170.1, 52.6, 49.8, 46.9, 31.9, 29.6, 29.6, 29.6, 29.3, 22.7, 19.4, 14.1; HRMS (ESI-TOF) nm/z calcd for C$_{12}$H$_{24}$N$_2$O [M+H]$^+$ 212.1889. found 212.1318.

Preparation of 3-N$_2$.

The primary alcohol of diazirine 5 was oxidized to the corresponding acid using standard Jones oxidation conditions. $^1$H NMR (400 MHz, CDCl$_3$, 25° C.): δ=2.28 (d, 2H, J=4.4 Hz), 1.53-1.51 (m, 2H), 1.26-1.17 (m, 14H), 0.84 (t, 3H, J=6.8 Hz); $^{13}$C NMR (100 MHz, DMSO, 25° C.): δ=177.3, 168.9, 52.4, 46.3, 31.9, 29.6, 29.6, 29.6, 29.3, 22.7, 19.1, 14.1; HRMS (ESI-TOF) m/z calcd for C$_{12}$H$_{22}$N$_2$O$_2$ [M+H]$^+$ 226.1681. found 226.1653. The acid was converted to the corresponding acid chloride using oxalyl chloride and coupled to (S)-α-Amino-γ-butyrolactone as previously described.[E7,E8] $^1$H NMR (400 MHz, CDCl$_3$, 25° C.): δ=6.24 (app s, 1H), 4.57-4.47 (m, 2H), 4.32-4.29 (m, 1H), 2.88-2.85 (m, 1H), 2.27-2.2 (m, 3H), 1.53 (t, 2H, J=6.8 Hz), 1.26-1.15 (m, 14H), 0.87 (t, 3H, J=6.8 Hz); $^{13}$C NMR (100 MHz, DMSO, 25° C.): δ=190.0, 175.4, 168.9, 66.3, 49.6, 41.4, 32.7, 29.6, 29.5, 29.4, 29.2, 24.0, 14.3, 14.2 (14 found); HRMS (ESI-TOF) m/z calcd for C$_{16}$H$_{27}$N$_3$O$_3$ [M+H]$^+$ 309.2052. found 309.2039.

C. Bacterial Experiments

Exposure of Cancer Cells to Bacterial Culture.

We utilized experimental systems in which products released by bacteria can interact with eukaryotic targets while avoiding direct contact of bacteria with cells in tissue culture. The inserts containing bacterial cultures were placed in close proximity to cultured lung cancer cells that were left untreated or treated with TRAIL (TRAIL was added directly into GM media at the same time). We used a custom fabricated insert prepared from cut polystyrene tubing (14 mm diameter×25 mm height) with a solvent-welded polyvinylidene fluoride membrane base (PVDF Durapore hydrophilic 0.1 m membrane, Millipore VVLP09050). To prepare these inserts, one end of the cut polystyrene tubing is dipped into methylene chloride for 5 seconds, and the softened plastic is pressed onto the surface of a cut section of PVDF membrane for 0.5 min. The softened polystyrene flows into the PVDF sufficiently to form an impervious bond without damaging the membrane pore structure. After allowing a few hours for the solvent to completely evaporate, inserts are immersed in 1% hypochlorite for 30 minutes followed by 6 rinses with sterile saline (performed in a laminar flow hood). The 14 mm diameter insert is an optimal fit for the 24-well plate, with the internal area of the insert covering ~70% of the well surface.

We used the prototype 0.1 μm PVDF membrane inserts for studies in which tissue culture cells are exposed to soluble products derived from P. aeruginosa PAO1 (wild type), PAO1 ΔlasI, S. aureus, S. typhimurium, A. baumannii and E. coli. The bacteria were grown on BHI agar plates, transferred to inoculum culture overnight followed by 1/100 dilution into 20 ml BHI broth in 125 ml baffled shake flasks for incubation at 37° C., 250 rpm for 4-6 hr. The equal aliquots of the late log phase culture or control BHI broth were transferred to PVDF inserts which were placed in 24-well plates containing target cells cultured in 0.5 ml DMEM growth medium.

Determination of C12 Concentration in Bacterial Cultures.

A 2-ml culture was acidified with 50 μl of HCl and 10 ml of ethyl acetate was added, and the contents were mixed vigorously. The layers were allowed to separate, and 5 ml of the ethyl acetate layer were removed, dried over MgSO$_4$, and concentrated in vacuo. The residue was resuspended in cold methanol and centrifuged to remove the precipitate. The resulting methanol solution was analyzed by LC-MS (liquid chromatography-mass spectrometry) for C12 content. Reverse phase LC-MS analysis (Agilent Zorbax column. 5 μm, 300SB-C8, 4.6×50 mm) was performed with gradients of MeCN—H2O-0.1% formic acid (from 0 to 1 min: 5% MeCN, from 1 min to 9 min: gradient of 5% MeCN to 98% MeCN, and from 9 to 11 min: 98% MeCN) allowing for quantification of C12 by measuring the following ions: 298 (M+H$^+$), 316 (M+H$_2$O+H$^+$), 320 (M+Na$^+$), and 338 (M+H$_2$O+Na$^+$). The concentration of C12 in the samples of

*P. aeruginosa* PAO1 (wild type) was about 4.3 µM (P<0.001, n=5 independent experiments).

D. Mammalian Cell Activation

Cell Stimulation.

In all experiments, BMDM were stimulated with LPS (100 ng/ml), AHL (10-25 µM; usually BMDM and primary macrophages were stimulated by 25 µM of C12) or their combination as indicated in the figure legends. If not indicated, cancer and normal cells were stimulated with 40 ng/ml of TNFα, 20 ng/ml TRAIL and 10 µM (in case of cancer cells) or 25 µM (in case of normal cells) of AHL.

E. Cell Viability and Assessment of Apoptosis

Cytotoxicity was determined by using the XTT-based toxicology assay kit (Sigma, St. Louis, Miss.) in accordance with the manufacturer's instructions. For some experiments, to confirm the apoptotic nature of toxicity, cells were analyzed using protocols and instructions of the Annexin V-FITC apoptosis detection kit (Biovision, Mountain View, Calif.). In addition, caspase 3, 8 and 9 activities were determined by colorimetric assays (R&D System), and the data are expressed as fold increases compared to the values of untreated or control-treated cells (n=5).

F. Experimental References Cited (E1) Mathison. J. C.; Virca, G. D.; Wolfson, E.; Tobias. P. S.; Glaser, K.; Ulevitch, R. J. *J. Clin. Invest.* 1990, 85, 1108.
(E2) Kaufmann, G. F.; Sartorio, R.; Lee, S. H.; Rogers, C. J.; Meijler, M. M.; Moss, J. A.; Clapham, B.; Brogan, A. P.; Dickerson, T. J.; Janda, K. D. *Proc. Natl. Acad. Sci., U.S.A* 2005, 102, 309.
(E3) Kravchenko, V. V.; Ulevitch, R. J.; Kaufmann, G. F. *Methods Mol. Biol.* 2010, 692, 133.
(E4) Langer, P.; Bellur, E. *J. Org. Chem.* 2003, 68, 9742.
(E5) Kirihara, M.; Kakuda, H.; Ichinose, M.; Ochiai, Y.; Takizawa, S.; Mokuya, A.; Okubo, K.; Hatano, A.; Shiro, M. *Tetrahedron* 2005, 61, 4831.
(E6) Church, R. F. R.; Weiss, M. J. *J. Org. Chem.* 1970, 35, 2465.
(E7) Kaufmann, G. F.; Sartorio, R.; Lee. S. H.; Mee, J. M.; Altobell, L. J., 3rd; Kujawa, D. P.; Jeffries, E.; Clapham, B.; Meijler, M. M.; Janda, K. D. *J. Am. Chem. Soc.* 2006, 128, 2802.
(E8) Garner, A. L.; Yu, J.; Struss, A. K.; Lowery, C. A.; Zhu, J.; Kim, S. K.; Park, J.; Mayorov, A. V.; Kaufmann, G. F.; Kravchenko, V. V.; Janda, K. D. *Bioorg. Med. Chem. Lett.* 2011, 21, 2702.

All patents and publications, patent and non-patent, referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A pharmaceutical composition comprising an effective amount of an N-acylhomoserine lactone (AHL) analog compound of formula (I):

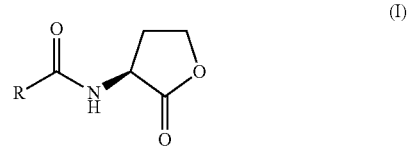

wherein R is a linear alkyl, alkenyl or alkynyl of about 9 to about 15 carbon atoms having one or more diazirenyl groups, optionally having one or more carbonyl groups at positions 4 or greater on the alkyl, alkenyl or alkynyl groups, and further optionally substituted with azido, hydroxyl, or halo; or a pharmaceutically acceptable salt thereof; and, optionally, a pharmaceutically acceptable excipient.

2. The pharmaceutical composition of claim 1, wherein the compound is of formula (II)

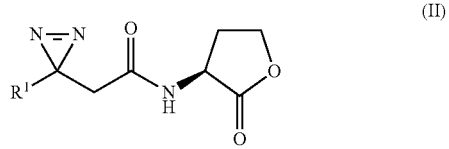

wherein $R^1$ is a linear alkyl, alkenyl or alkynyl of about 7 to 13 carbon atoms, optionally having one or more of:
a diazirenyl group;
one or more carbonyl groups; or
one or more independently selected azido, hydroxyl, or halo groups.

3. The pharmaceutical composition of claim 1, further comprising a tumor modulating agent that is a TRAIL polypeptide.

4. The pharmaceutical composition of claim 1, wherein the N-acylhomoserine lactone (AHL) analog is selected from the group consisting of:

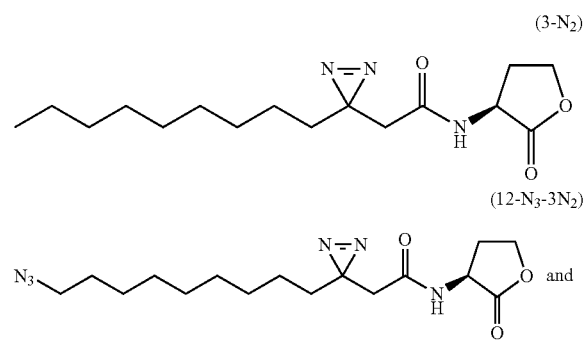

(12-N₃-6-N₂-12)

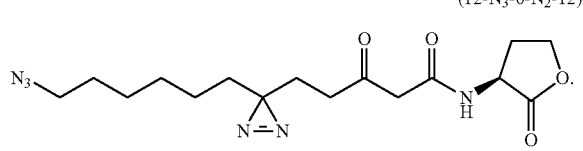

5. A method of treating a tumor in a patient, comprising administering to the patient an effective amount of an N-acylhomoserine lactone (AHL) analog compound of formula (I)

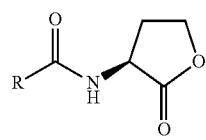

(I)

wherein R is a linear alkyl, alkenyl or alkynyl of about 9 to about 15 carbon atoms having one or more diazirenyl groups, optionally having one or more carbonyl groups, and further optionally substituted with azido, hydroxyl, or halo; or a pharmaceutically acceptable salt; and optionally, a pharmaceutically acceptable excipient, wherein the tumor is selected from the group consisting of lung, cervical, breast, and brain tumors.

6. The method of treating a tumor in a patient of claim 5, wherein the compound is a compound of formula (II)

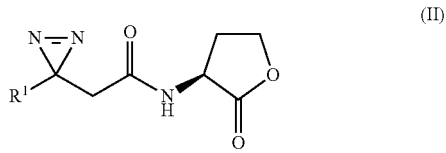

(II)

wherein R¹ is a linear alkyl, alkenyl or alkynyl of about 7 to 13 carbon atoms, optionally having one or more of:
a diazirenyl group;
one or more carbonyl groups; or
one or more independently selected azido, hydroxyl, or halo groups.

7. The method of treating a tumor in a patient of claim 5, further comprising administering an effective amount of a tumor modulating agent that is a TRAIL polypeptide.

8. The method of treating a tumor in a patient of claim 5, wherein the N-acylhomoserine lactone (AHL) analog is selected from the group consisting of:

(3-N₂)

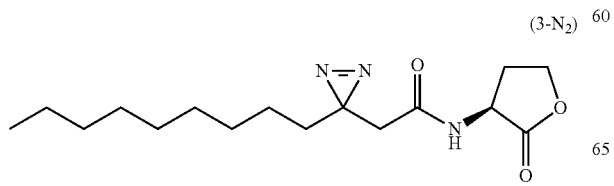

(12-N₃-3N₂)

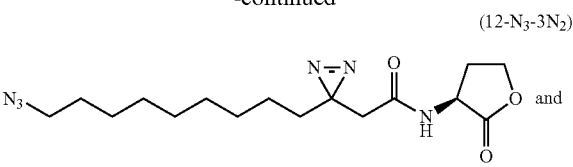

and (12-N₃-6-N₂-12)

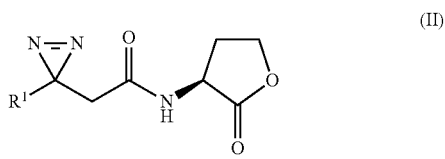

9. A compound of formula (I):

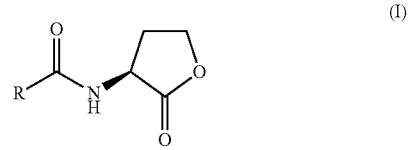

(I)

wherein R is a linear alkyl, alkenyl or alkynyl of about 9 to about 15 carbon atoms having one or more diazirenyl groups, optionally having one or more carbonyl groups at positions 4 or greater on the alkyl, alkenyl or alkynyl groups, and further optionally substituted with azido, hydroxyl, or halo; or, a pharmaceutically acceptable salt thereof.

10. The compound of claim 9, wherein the compound is a compound of formula (II)

(II)

wherein R¹ is a linear alkyl, alkenyl or alkynyl of about 7 to 13 carbon atoms, optionally having one or more of:
a diazirenyl group;
one or more carbonyl groups; or
one or more independently selected azido, hydroxyl, or halo groups.

11. The compound of claim 9, in a pharmaceutical combination with a tumor modulating agent that is a TRAIL polypeptide.

12. The compound of claim 9, wherein the N-acylhomoserine lactone (AHL) analog is selected from the group consisting of:

(3-N₂)

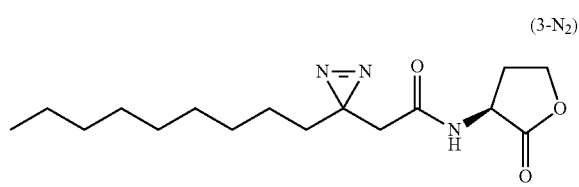

-continued

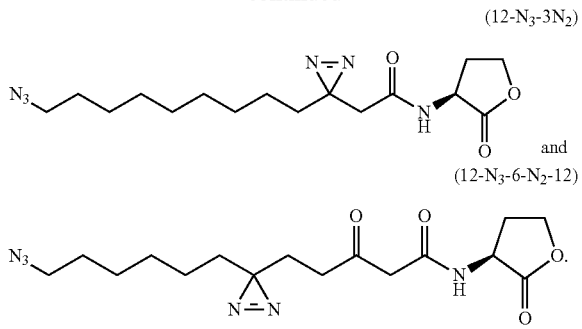
(12-N₃-3N₂)

and (12-N₃-6-N₂-12)

13. A method for inducing apoptosis, arrest of cell division, or inhibition of cell proliferation, in a tumor cell, comprising contacting the cell with an effective amount of an N-acylhomoserine lactone (AHL) compound, and an effective amount of a TRAIL, wherein the AHL compound is of formula (I):

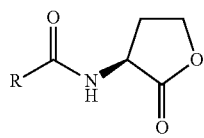
(I)

wherein R is a linear alkyl, alkenyl or alkynyl of about 9 to about 15 carbon atoms having one or more diazirenyl groups, optionally having one or more carbonyl groups, and further optionally substituted with azido, hydroxyl, or halo, wherein the tumor cell is selected from the group consisting of lung tumor cells, cervical tumor cells, breast tumor cells, and brain tumor cells.

14. The method for inducing apoptosis, arrest of cell division, or inhibition of cell proliferation, in a tumor cell, of claim 13 wherein the AHL analog in the effective amount is an activator of the unfolded protein response (UPR), of endoplasmic reticulum swelling (ERS), or both, in the tumor cell.

15. The method for inducing apoptosis, arrest of cell division, or inhibition of cell proliferation, in a tumor cell, of claim 13 wherein the compound is a compound of formula (II)

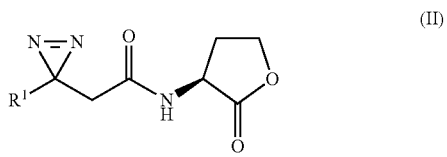
(II)

wherein R¹ is a linear alkyl, alkenyl or alkynyl of about 7 to 13 carbon atoms, optionally having one or more of:
a diazirenyl group;
one or more carbonyl groups; and
one or more independently selected azido, hydroxyl, or halo groups.

16. The method for inducing apoptosis, arrest of cell division, or inhibition of cell proliferation, in a tumor cell, of claim 13 wherein the N-acylhomoserine lactone (AHL) analog is selected from the group consisting of:

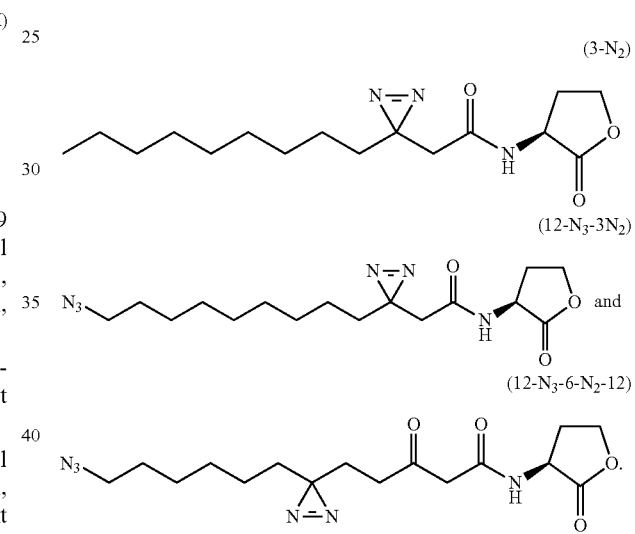
(3-N₂)

(12-N₃-3N₂)

and (12-N₃-6-N₂-12)

* * * * *

UNITED STATES PATENT AND TRADEMARK OFFICE
CERTIFICATE OF CORRECTION

PATENT NO.       : 9,604,950 B2
APPLICATION NO.  : 14/778327
DATED            : March 28, 2017
INVENTOR(S)      : Kravchenko et al.

Page 1 of 3

It is certified that error appears in the above-identified patent and that said Letters Patent is hereby corrected as shown below:

In Column 3, Line 58, delete "container," and insert --container;-- therefor

In Column 3, Line 66, delete "Induces" and insert --induces-- therefor

In Column 4, Line 1, delete "tvphimurium" and insert --typhimurium-- therefor

In Column 4, Line 26, delete "Induces" and insert --induces-- therefor

In Column 6, Line 50, delete "-C(CH$_2$CH$_3$)-CH$_2$," and insert -- -C(CH$_2$CH$_3$)=CH$_2$,-- therefor In Column 15, Line 33-38, delete " 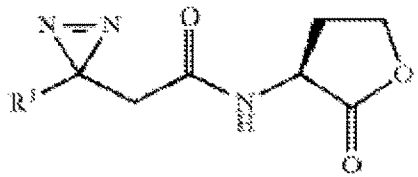 " and insert 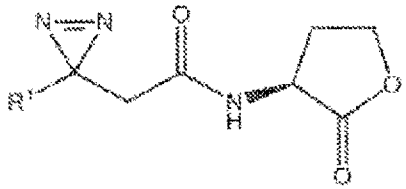 -- -- therefor In Column 28, Line 7, delete "Staphylooccus" and insert --Staphylococcus-- therefor In Column 29, Line 14, delete "eIF2α(FIG. 2B)." and insert --eIF2α (FIG. 2B).-- therefor In Column 29, Line 41, delete "Sph." and insert --Sph,-- therefor In Column 30, Line 21, delete "SIP" and insert --S1P-- therefor Signed and Sealed this
Eighteenth Day of September, 2018

Andrei Iancu
*Director of the United States Patent and Trademark Office*

CERTIFICATE OF CORRECTION (continued)
U.S. Pat. No. 9,604,950 B2

In Column 32, Line 2, delete "cells[28](Ashkenazi" and insert --cells[28] (Ashkenazi-- therefor In Column 32, Line 11, delete "(25 M)" and insert --(25 μM)-- therefor In Column 33, Line 49, delete "Medzhitov." and insert --Medzhitov,-- therefor In Column 34, Line 14, delete "Nisbet." and insert --Nisbet,-- therefor In Column 34, Line 21, delete "Hughes." and insert --Hughes,-- therefor In Column 34, Line 53, delete "Biophvs" and insert --Biophys-- therefor In Column 34, Line 63, delete "All," and insert --Ali,-- therefor In Column 35, Line 15, delete "Jones." and insert --Jones,-- therefor In Column 35, Line 22, delete "Holland." and insert --Holland,-- therefor In Column 36, Line 21, delete "Singh." and insert --Singh,-- therefor In Column 36, Line 31, delete "Inject" and insert --Infect-- therefor In Column 36, Line 44, delete "Mohle-Steinlein." and insert --Mohle-Steinlein,-- therefor In Column 36, Line 50, delete "(6)." and insert --(6),-- therefor In Column 43, Line 2, delete "ryphimurium," and insert --typhimurium,-- therefor In Column 43, Line 20, delete "-20° C." and insert -- -20 °C.-- therefor In Column 44, Line 53, delete "25° C." and insert --25 °C.-- therefor In Column 44, Line 57, delete "25° C." and insert --25 °C.-- therefor In Column 45, Line 21, delete "25° C." and insert --25 °C.-- therefor In Column 45, Line 24, delete "25° C." and insert --25 °C.-- therefor In Column 45, Line 57, delete "212.1889." and insert --212.1889,-- therefor In Column 45, Line 66, delete "226.1681." and insert --226.1681,-- therefor In Column 46, Line 9, delete "309.2052." and insert --309.2052,-- therefor In Column 46, Line 60-61, delete "column." and insert --column,-- therefor

CERTIFICATE OF CORRECTION (continued)
U.S. Pat. No. 9,604,950 B2

In Column 46, Line 62, delete "MeCN-H2O-0.1%" and insert --MeCN-$H_2$O-0.1%-- therefor In Column 47, Line 30, delete "Mathison." and insert --Mathison,-- therefor In Column 47, Line 30, delete "Tobias." and insert --Tobias,-- therefor In Column 47, Line 44, delete "Lee." and insert --Lee,-- therefor

UNITED STATES PATENT AND TRADEMARK OFFICE
CERTIFICATE OF CORRECTION

| | |
|---|---|
| PATENT NO. | : 9,604,950 B2 |
| APPLICATION NO. | : 14/778327 |
| DATED | : March 28, 2017 |
| INVENTOR(S) | : Kravchenko et al. |

Page 1 of 1

It is certified that error appears in the above-identified patent and that said Letters Patent is hereby corrected as shown below:

In the Specification

Column 1, Lines 17-22, the paragraph STATEMENT OF GOVERNMENT SUPPORT should be changed to:
-- STATEMENT OF GOVERNMENT LICENSE RIGHTS
This invention was made with government support under grant numbers AI077644, AI079436, AI094348 and contract number HHSN272200700038C awarded by the National Institutes of Health. The government has certain rights in the invention. --

Signed and Sealed this
Fifth Day of May, 2020

Andrei Iancu
*Director of the United States Patent and Trademark Office*